(12) United States Patent
Matsumoto

(10) Patent No.: US 9,495,776 B2
(45) Date of Patent: Nov. 15, 2016

(54) COMPUTING METHOD AND COMPUTING APPARATUS

(75) Inventor: Kazuhiro Matsumoto, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 66 days.

(21) Appl. No.: 13/606,991

(22) Filed: Sep. 7, 2012

(65) Prior Publication Data

US 2013/0076752 A1    Mar. 28, 2013

(30) Foreign Application Priority Data

Sep. 28, 2011   (JP) .................. 2011-212263

(51) Int. Cl.
| | |
|---|---|
| G06T 11/20 | (2006.01) |
| G06Q 10/04 | (2012.01) |
| G06Q 50/04 | (2012.01) |
| G06Q 10/00 | (2012.01) |
| G06F 19/00 | (2011.01) |
| G06F 17/00 | (2006.01) |

(52) U.S. Cl.
CPC ............. *G06T 11/206* (2013.01); *G06Q 10/04* (2013.01); *G06Q 50/04* (2013.01); *G06F 17/00* (2013.01); *G06F 19/706* (2013.01); *G06F 19/707* (2013.01); *G06Q 10/00* (2013.01); *G06T 11/20* (2013.01); *Y02P 90/30* (2015.11)

(58) Field of Classification Search
USPC ....................................................... 345/440
See application file for complete search history.

(56) References Cited

U.S. PATENT DOCUMENTS

| | | | |
|---|---|---|---|
| 2005/0131847 A1* | 6/2005 | Weston et al. ............ | 706/12 |
| 2008/0288445 A1* | 11/2008 | Ames et al. ............... | 707/2 |
| 2009/0273602 A1* | 11/2009 | Wong et al. .............. | 345/440 |
| 2009/0326875 A1 | 12/2009 | Yanami et al. | |
| 2011/0077916 A1* | 3/2011 | Cohn et al. .............. | 703/2 |
| 2011/0112811 A1 | 5/2011 | Matsumoto | |

FOREIGN PATENT DOCUMENTS

| | | |
|---|---|---|
| JP | 2001-52041 A | 2/2001 |
| JP | 2005-70849 | 3/2005 |

(Continued)

OTHER PUBLICATIONS

Edwin D. de Jong, Objective Fitness Correlation, Jul. 7, 2007, ACM,978-1-59593-697-4/07/0007, 442-445.*

(Continued)

*Primary Examiner* — Mark Zimmerman
*Assistant Examiner* — Yu-Jang Tswei
(74) *Attorney, Agent, or Firm* — Fujitsu Patent Center

(57) ABSTRACT

In a computing apparatus, a computing unit performs statistical analysis on data including the values of a plurality of input variables and the values of a plurality of output variables optimized by adjusting the values of the plurality of input variables, thereby generating the values of intermediate variables that indicate relative positional relationship among the values of each of the plurality of input variables and the plurality of output variables. The creation unit creates scatter diagrams representing the tendency of magnitude relationship among values of a variable, by using the generated values of the intermediate variables, for the respective input variables and output variables. The display unit displays the created scatter diagrams.

1 Claim, 30 Drawing Sheets

(56) References Cited

FOREIGN PATENT DOCUMENTS

| | | |
|---|---|---|
| JP | 2005-284470 | 10/2005 |
| JP | 2005-352637 | 12/2005 |
| JP | 2007-253495 | 10/2007 |
| JP | 2008-192076 A | 8/2008 |
| JP | 2009-66088 A | 4/2009 |
| JP | 2010-9341 A | 1/2010 |
| JP | 2010-042599 | 2/2010 |
| JP | 2011-103067 | 5/2011 |

OTHER PUBLICATIONS

Wayback ("Pearson product-moment correlation coefficient", Sep. 17, 2011, WaybackMachine).*
Japanese Office Action mailed Mar. 31, 2015 for corresponding Japanese Patent Application No. 2011-212263, with Partial English Translation, 8 pages.
Clarich, Alberto et al.,"Multi-Objective Optimization With Modefrontier Interfaces for ANSA and Metapost", Jun. 1, 2011, BETA CAE Systems S.A., 4th ANSA & μETA International Conference Proceedings, Greek, [Searched: Feb. 23, 2015], Internet <URL:http://www.beta.cae.gr/events/c4pdf/7B_3_clarich.pdf>, 16 pages.
Ishiguro, Hidetaka et al.,"Visualization of Relationships between Genes and Evaluation Values in GA and Feedback into Genetic Operations", Journal of Japan Society for Fuzzy Theory and Intelligent Informatics, Japan Society for Fuzzy Theory and Intelligent Informatics, Jun. 15, 2009, vol. 21 No. 3, pp. 327-337, Feature: Visualization: knowledge acquisition techniques from multi-dimensional data, English Abstract on p. 337 and see JPOA filed herewith.

* cited by examiner

| | LENGTH | WIDTH | CRASH SAFETY | FUEL EFFICIENCY |
|---|---|---|---|---|
| RECORD 1 | 10 | 20 | 30 | 40 |
| RECORD 2 | ... | ... | ... | ... |
| RECORD 3 | ... | ... | ... | ... |

DATA 13a

INPUT VARIABLE (LENGTH, WIDTH) — OUTPUT VARIABLE (CRASH SAFETY, FUEL EFFICIENCY)

FIG. 4

| RECORD | INTERMEDIATE VARIABLE 1 OF RECORD 1 | INTERMEDIATE VARIABLE 2 OF RECORD 1 | ... | INTERMEDIATE VARIABLE 1 OF RECORD 2 | INTERMEDIATE VARIABLE 2 OF RECORD 2 | ... | INTERMEDIATE VARIABLE N5 OF RECORD N4 |
|---|---|---|---|---|---|---|---|
| | ... | ... | ... | ... | ... | ... | ... |

FIG. 13

COMPUTING METHOD AND COMPUTING APPARATUS

CROSS-REFERENCE TO RELATED APPLICATION

This application is based upon and claims the benefit of priority of the prior Japanese Patent Application No. 2011-212263, filed on Sep. 28, 2011, the entire contents of which are incorporated herein by reference.

FIELD

The embodiments discussed herein relate to a computing method and computing apparatus.

BACKGROUND

In product development for developing a high performance product at a low cost, assume that the first objective is to improve the performance of the product and the second objective is to minimize the cost of the product. When the development is attempting to improve the first objective (i.e., improve performance), the second objective suffers (i.e., cost becomes higher). Conversely, when the development is attempting to improve the second objective (i.e., reduce cost), the first objective suffers (i.e., performance degrades). In this way, the first and second objectives cannot be improved together and are in conflicting relationship, and this relationship is called "trade-off relationship". To improve a plurality of objectives having the trade-off relationship, multi-objective optimization techniques are well known. Please see, for example, Japanese Laid-open patent Publications Nos. 2005-70849 and 2011-103067.

Some of the known methods for displaying the results of multi-objective optimization include a scatter diagram matrix in which scatter diagrams for all different combinations of input and output variables are arranged in matrix, and a parallel coordinate plot where a horizontal axis represents input and output variables and a vertical axis represents the values of the input and output variables.

A user narrows down the values of input variables to ranges that are expected to yield user-desired values of output variables, from a scatter diagram matrix or a parallel coordinate plot, and runs a simulation within the determined ranges in order to obtain the values of the output variables corresponding to the values of the input variables falling within the determined ranges. The user is able to confirm whether the values of the output variables obtained from the values of the input variables in the determined ranges are user-desired values or not.

However, as the number of input and output variables increases, it becomes more difficult to interpret the relationships among input and output variables from a scatter diagram matrix or a parallel coordinate plot.

SUMMARY

According to one aspect, there is provided a computing method. This computing method includes: performing statistical analysis on data including values of a plurality of input variables and values of a plurality of output variables optimized by adjusting the values of the plurality of input variables, in order to generate values of intermediate variables that indicate relative positional relationship among the values of each of the plurality of input variables and the plurality of output variables; creating, for each of the input variables and output variables, a diagram representing tendency of magnitude relationship among values of the variable by using the generated values of the intermediate variables; and displaying the created diagrams.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 illustrates an example of data generated by a data generation unit;

FIGS. 13 to 16 illustrate an example of data generated through the process of FIG. 12;

DESCRIPTION OF EMBODIMENTS

Figure 1:
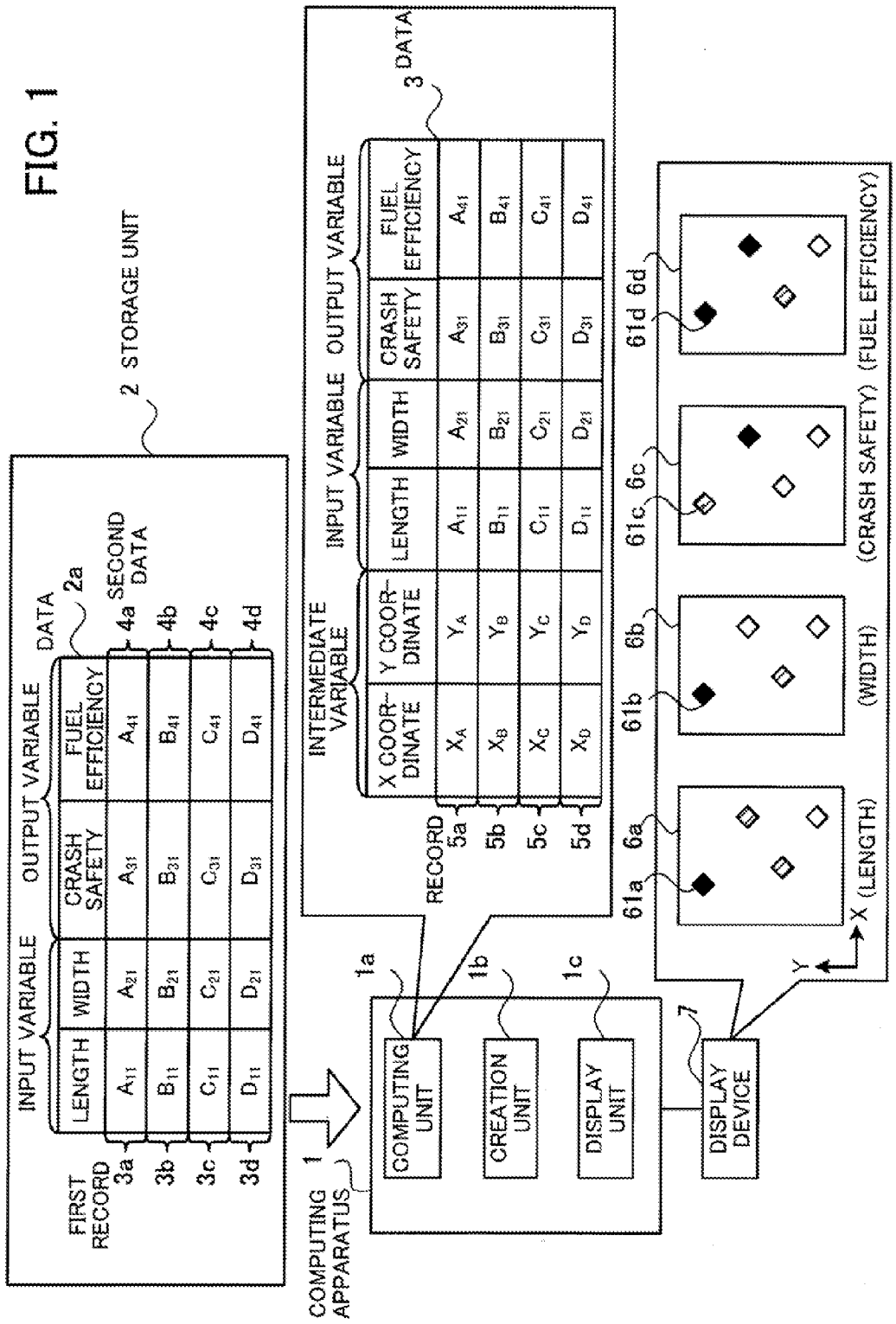
FIG. 1 is a diagram explaining a computing apparatus according to a first embodiment.

The computing apparatuses according to several embodiments will be described below with reference to the accompanying drawings, wherein like reference numerals refer to like elements throughout.

(A) First Embodiment

FIG. 1 is a diagram explaining a computing apparatus according to the first embodiment.

A computing apparatus (computer) 1 according to the first embodiment includes a computing unit 1a, creation unit 1b, and display unit 1c. These computing unit 1a, creation unit 1b, and display unit 1c are realized as the functions of a Central Processing Unit (CPU) provided in the computing apparatus 1.

The computing unit 1a reads data 2a from a storage unit 2. The data 2a includes the values of input variables "length" and "width", and the values of output variables "crash safety" and "fuel efficiency" which are optimized by adjusting the values of the input variables. This data 2a includes first records 3a, 3b, 3c, and 3d each made up of the values of the two input variables, and second records 4a, 4b, 4c, and 4d each made up of the values of the two output variables generated based on the corresponding first records 3a, 3b, 3c, and 3d. In this connection, a method of optimizing the values of output variables will be described in detail later in a second embodiment.

The storage unit 2 is realized by using a Random Access Memory (RAM) or Hard Disk Drive (HDD). In this embodiment, the computing unit 1a reads the data 2a previously stored in the storage unit 2, but may be designed to generate the data 2a. In addition, the storage unit 2 may be provided in the computing apparatus 1.

The computing unit 1a performs statistical analysis to generate the values of intermediate variables that represent relationships indicated by the data 2a, with two variables that are less than a total number of four, i.e., two input variables and two output variables included in the data 2a.

As a statistical analysis method, a method of projecting high-dimensional data to a lower-dimensional space may be used. Such methods include, for example, Multi-Dimensional Scaling (MDS), Sammon mapping, Singular Value Decomposition (SVD), Neural Network, Kernel Principal Component Analysis (KPCA), etc. This embodiment employs statistical analysis using the multi-dimensional scaling in order to generate the values of intermediate variables by way of example.

The computing unit 1a calculates a degree of dissimilarity between the first record 3a and the second record 4a by using, for example, Pearson's correlation coefficient. The calculated degree of dissimilarity is converted into distance data by using a publicly-known method. Then, the computing unit 1a obtains the coordinates $(X_A, Y_A)$ of a point in the two dimensional space from the obtained distance data. The obtained X and Y coordinates are the values of intermediate variables with respect to the values of the input variables of the first record 3a and the values of the output variables of the second record 4a.

The computing unit 1a generates a record 5a associating the obtained X and Y coordinates of the point with the first record 3a and second record 4a. The computing unit 1a also generates records 5b, 5c, and 5d by processing the first record 3b and second record 4b, the first record 3c and second record 4c, and the first record 3d and second record 4d, respectively, in the same way. Then, the computing unit 1a generates and stores data 3 including the records 5a, 5b, 5c, and 5d.

The creation unit 1b creates scatter diagrams 6a, 6b, 6c, and 6d which represent the tendency of magnitude relationship among values of input and output variables, from the data 3 generated by the computing unit 1a. More specifically, the creation unit 1b creates formats for scatter diagrams regarding the input variables "length" and "width" and the output variables "crash safety" and "fuel efficiency". The coordinate system of the formats for the scatter diagrams is the same as that of the two dimensional space obtained by the computing unit 1a.

Then, the creation unit 1b plots samples at X and Y coordinates indicated by the records 5a, 5b, 5c, and 5d in the created formats. For example, the creation unit 1b plots a sample 61a at coordinates $(X_A, Y_A)$ indicated by the record 5a in one format, plots a sample 61b at coordinates $(X_B, Y_B)$ indicated by the record 5b in one format, plots a sample 61c at coordinates $(X_C, Y_C)$ indicated by the record 5c in one format, and plots a sample 61d at coordinates $(X_D, Y_D)$ indicated by the record 5d in one format. Then, the creation unit 1b determines a pattern for indicating the magnitude of the value of each plotted sample on the basis of the value of a corresponding input or output variable. For example, a sample is blacked out if a value is less than 10, diagonal lines are drawn in a sample if a value is 10 or greater and less than 20, and a sample is outlined if a value is 20 or greater. Referring to FIG. 1, the sample 61a is blacked out according to the value "$A_{11}$" of the input variable "length".

The display unit 1c displays the scatter diagrams 6a, 6b, 6c, and 6d created by the creation unit 1c on a display device 7 connected to the computing apparatus 1.

In the above computing apparatus 1, the computing unit 1a generates data 3 including intermediate variables, by applying the multi-dimensional scaling to the data 2a indicating the results of multi-objective optimization. Then, the creation unit 1b creates scatter diagrams 6a, 6b, 6c, and 6d using the data 3.

The scatter diagrams 6a, 6b, 6c, and 6d enable a user to recognize the tendency of the data 2a easier compared with the case of scatter diagrams directly created from the data 2a (without generating the data 3). More specifically, from the scatter diagrams 6a, 6b, 6c, and 6d, the user is able to recognize that a longer length and longer width increase the value of crash safety (improves crash safety) but also increase the value of fuel efficiency (reduces fuel efficiency).

In this embodiment, the computing unit 1a obtains two-dimensional coordinates from distance data obtained by converting a degree of dissimilarity, but may be designed to obtain three-dimensional coordinates. In this case, X, Y, and Z coordinates are obtained as the values of intermediate variables for the values of the input variables included in the first record 3a and the values of the output variables included in the second record 4a.

Further, this embodiment uses different colors for samples to indicate the tendency of data. Alternatively, different shapes may be used for samples to indicate the tendency of data.

The following describes the computing apparatus in more detail as the second embodiment.

(B) Second Embodiment

Figure 2:
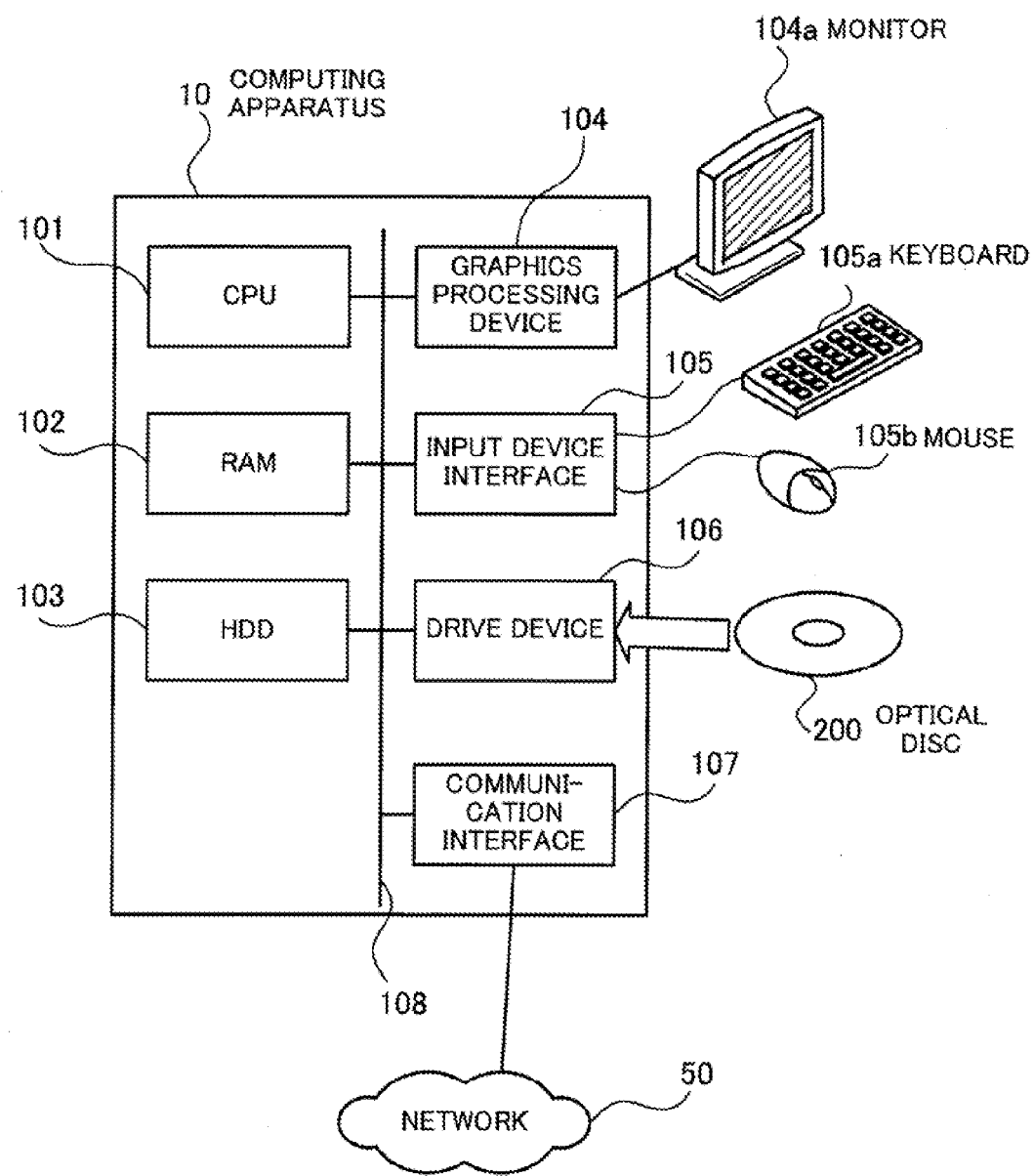
FIG. 2 illustrates hardware components of a computing apparatus according to a second embodiment.

FIG. 2 illustrates hardware components of a computing apparatus according to the second embodiment.

A computing apparatus 10 is entirely controlled by a CPU 101. A RAM 102 and a plurality of peripheral devices are connected to the CPU 101 via a bus 108.

The RAM 102 is used as a main memory device of the computing apparatus 10. The RAM 102 temporarily stores at least part of Operating System (OS) programs and application programs to be executed by the CPU 101. The RAM 102 also stores various data to be used while the CPU 101 operates.

Connected to the bus 108 are a hard disk drive (HDD) 103, graphics processing device 104, input device interface 105, drive device 106, and communication interface 107.

The HDD 103 magnetically writes and reads data on an internal disk. The HDD 103 is used as a secondary storage device of the computing apparatus 10. The HDD 103 stores the OS programs, application programs, and various data. In this connection, a flash memory or another kind of semiconductor storage device may be used as a secondary storage device.

A monitor 104a is connected to the graphics processing device 104. The graphics processing device 104 displays an image on the screen of the monitor 104a under the control of the CPU 101. As the monitor 104a, a display device using Cathode Ray Tube (CRT) or a liquid crystal display device may be used.

A keyboard 105a and mouse 105b are connected to the input device interface 105. The input device interface 105 transfers signals from the keyboard 105a and mouse 105b to the CPU 101. The mouse 105b is one example of a pointing device, and another kind of pointing device such as a touch panel, tablet, touchpad, or trackball may be used.

The drive device 106 reads data from an optical disc. The optical disc is a portable recording medium such as a Universal Serial Bus (USB) memory on which data is recorded so as to be read with reflection of light. For example, when an optical drive device is used as the drive device 106, data is read from an optical disc 200 using laser light. Optical discs 200 include Blu-ray (registered trademark), Digital Versatile Disc (DVD), DVD-RAM, Compact Disc Read Only Memory (CD-ROM), CD-R (Readable)/RW (ReWritable), etc.

The communication interface 107 is connected to a network 50. The communication interface 107 performs data communications with another computer or communication apparatus via the network 50.

The processing functions of this embodiment are realized by using the above hardware components.

The computing apparatus 10 having the hardware components of FIG. 2 is provided with the following functions.

Figure 3:
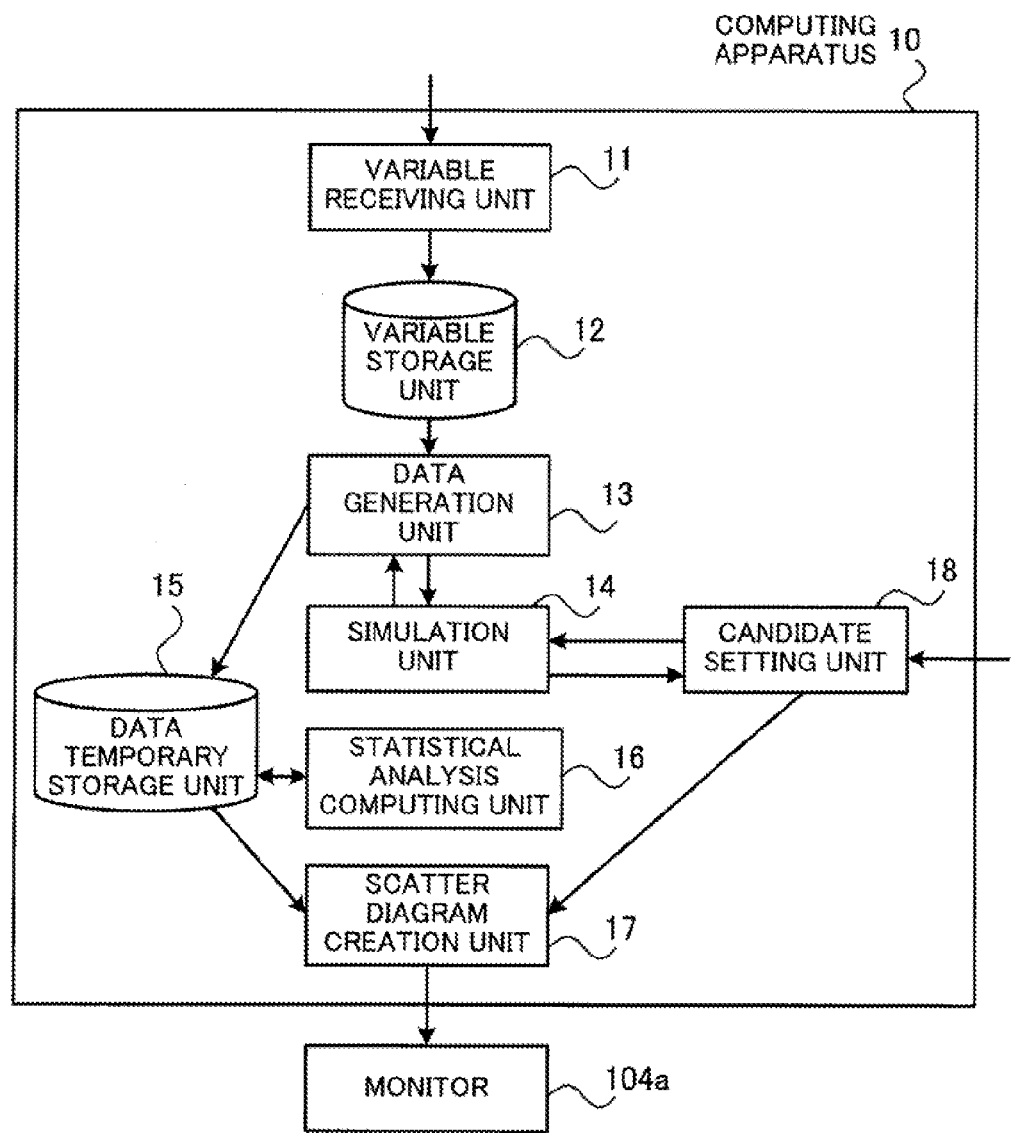
FIG. 3 is a functional block diagram of the computing apparatus according to the second embodiment.

FIG. 3 is a functional block diagram of the computing apparatus according to the second embodiment.

The computing apparatus 10 includes a variable receiving unit 11, variable storage unit 12, data generation unit 13, simulation unit 14, data temporary storage unit 15, statistical analysis computing unit 16, scatter diagram creation unit 17, and candidate setting unit 18.

The variable receiving unit 11 receives input variables and output variables in accordance with inputs made by the user of the computing apparatus 10. For example, in the case of automobile manufacturing, input variables may be length and width, and output variables may be crash safety and fuel efficiency.

The variable storage unit 12 stores input variables and output variables received by the variable receiving unit 11.

The data generation unit 13 generates the values of the input and output variables with respect to the input and output variables stored in the variable storage unit 12, and generates data having a plurality of records regarding the values of the input and output variables by applying an optimization algorithm to the generated values of the input variables. The optimization algorithm may be Nelder-Mead algorithm, Powell algorithm, genetic algorithm, simulated annealing algorithm, differential evolution algorithm, particle swarm optimization algorithm, or another algorithm.

FIG. 4 illustrates an example of data generated by the data generation unit.

Data 13a is an example of data generated by the data generation unit 13. The data 13a illustrated in FIG. 4 is data on two input variables and two output variables, and includes three records which have different values of each of the input variables and output variables.

Referring back to FIG. 3, the data generation unit 13 makes a simulation instruction to the simulation unit 14 when generating the data 13a.

The simulation unit 14 runs a computer simulation with data regarding the input variables generated by the data generation unit 13 in response to the received simulation instruction. Then, the simulation unit 14 returns the result of the computer simulation as data regarding the output variables corresponding to the input variables to the data generation unit 13.

The data temporary storage unit 15 temporarily stores the data 13a generated by the data generation unit 13, data regarding the output variables generated by the simulation unit 14, etc.

The statistical analysis computing unit 16 generates the values of intermediate variables which represent relationships indicated by the data generated by the data generation unit 13, with fewer variables than the total number of input variables and output variables included in the data generated by the data generation unit by executing statistical analysis computation. For example, the statistical analysis computing unit 16 generates the values of intermediate variables that represent the relationships indicated by the data 13a, with two variables that are less than a total number of four, i.e., two input variables and two output variables included in the data 13a. These intermediate variables are information that indicates arrangement positions where the input variables and output variables included in the data generated by the data generation unit 13 are to be plotted in scatter diagrams.

As a statistical analysis method, a method of projecting high-dimensional data to a lower-dimensional space may be used. Such methods include, for example, Multi-Dimensional Scaling, Sammon mapping, Singular Value Decomposition, Neural Network, Kernel Principal Component Analysis, etc. This embodiment employs statistical analysis using the multi-dimensional scaling by way of example.

The scatter diagram creation unit 17 creates scatter diagrams based on the data 13a generated by the data generation unit 13 and the values of the intermediate variables generated by the statistical analysis computing unit 16.

Figure 5:
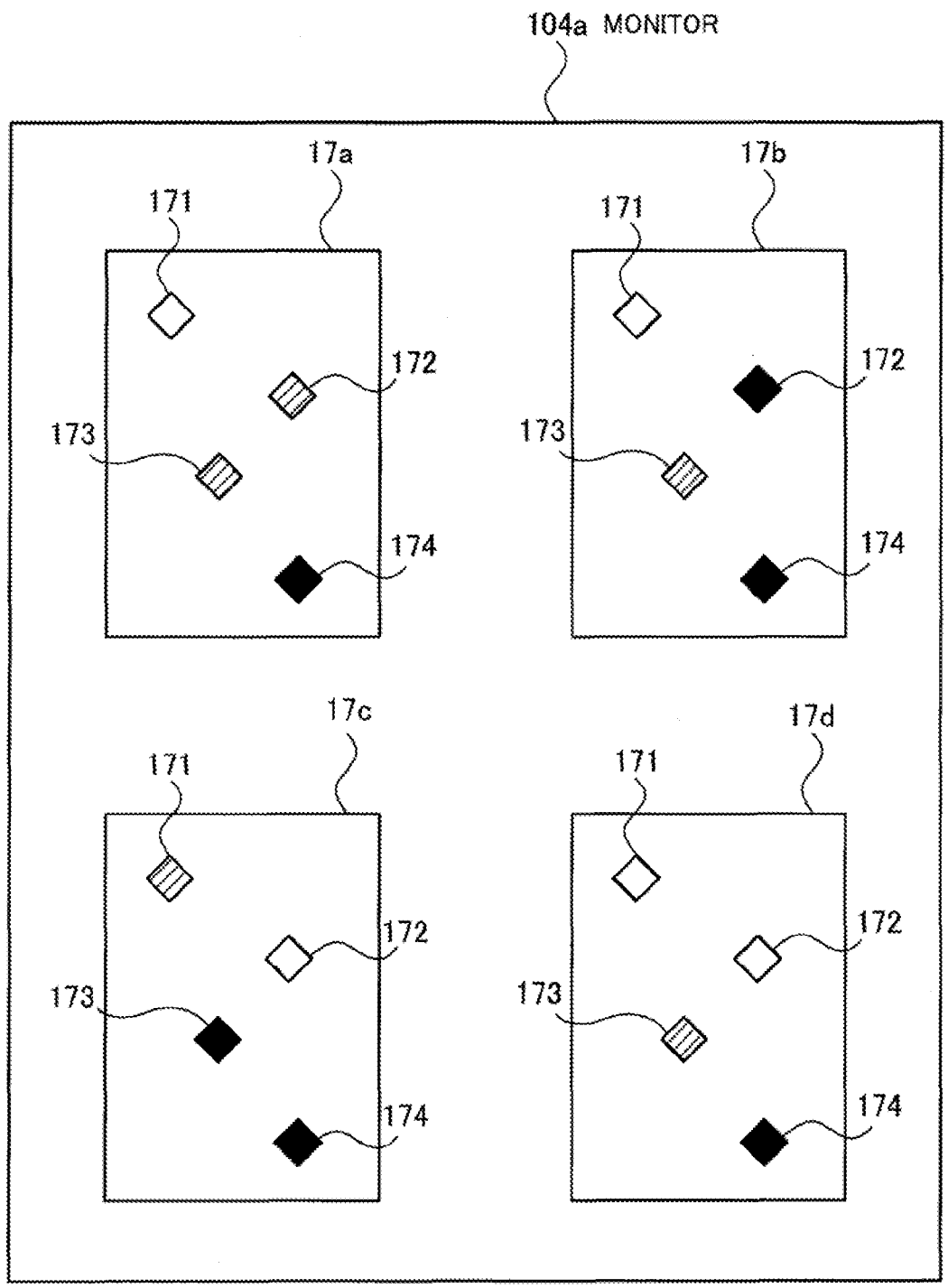
FIG. 5 illustrates an example of scatter diagrams created by a scatter diagram creation unit.

FIG. 5 illustrates an example of scatter diagrams created by the scatter diagram creation unit 17.

Scatter diagrams 17a, 17b, 17c, and 17d use parameters relating to the shape of a vehicle as input variables and parameters relating to the performance of the vehicle as output variables by way of example.

The scatter diagrams 17a and 17b illustrated in FIG. 5 relate to input variables "length" and "width", respectively, and the scatter diagrams 17c and 17d relate to output variables "crash safety" and "fuel efficiency", respectively.

Each of the samples 171, 172, 173, and 174 displayed in the scatter diagrams 17a, 17b, 17c, and 17d represents a value of a variable of a record generated by the data generation unit 13 (one piece of data). More specifically, the samples 171, 172, 173, and 174 represent the values of the respective variables of the records 1, 2, 3, and 4. The samples with the same codes are plotted in the same positions in these scatter diagrams 17a, 17b, 17c, and 17d.

The samples 171, 172, 173, and 174 are colored according to the magnitude of the values of variables. Referring to FIG. 5, samples whose values of the corresponding variables are lower than a first threshold are outlined, samples whose values of the corresponding variables are equal to or greater than the first threshold and lower than a second threshold are represented with diagonal lines, and samples whose values of the corresponding variables are equal to or greater than the second threshold are blacked out. In FIG. 5, the magnitudes of the values of data are represented by different colors, but may be represented by different shapes instead.

In the case where there are many input variables and many output variables, the scatter diagrams 17a, 17b, 17c, and 17d created for the respective variables enable a user to easily recognize the results of multi-objective optimization, i.e., the relationship among the input and output variables.

For example, the user is able to recognize from the scatter diagrams 17c and 17d that samples in the lower right side of the scatter diagram 17c indicate high crash safety and samples in the upper right side of the scatter diagram 17d indicate good fuel efficiency. The user is also able to recognize that a longer length and longer width increase crash safety but lower fuel efficiency.

Figure 6:
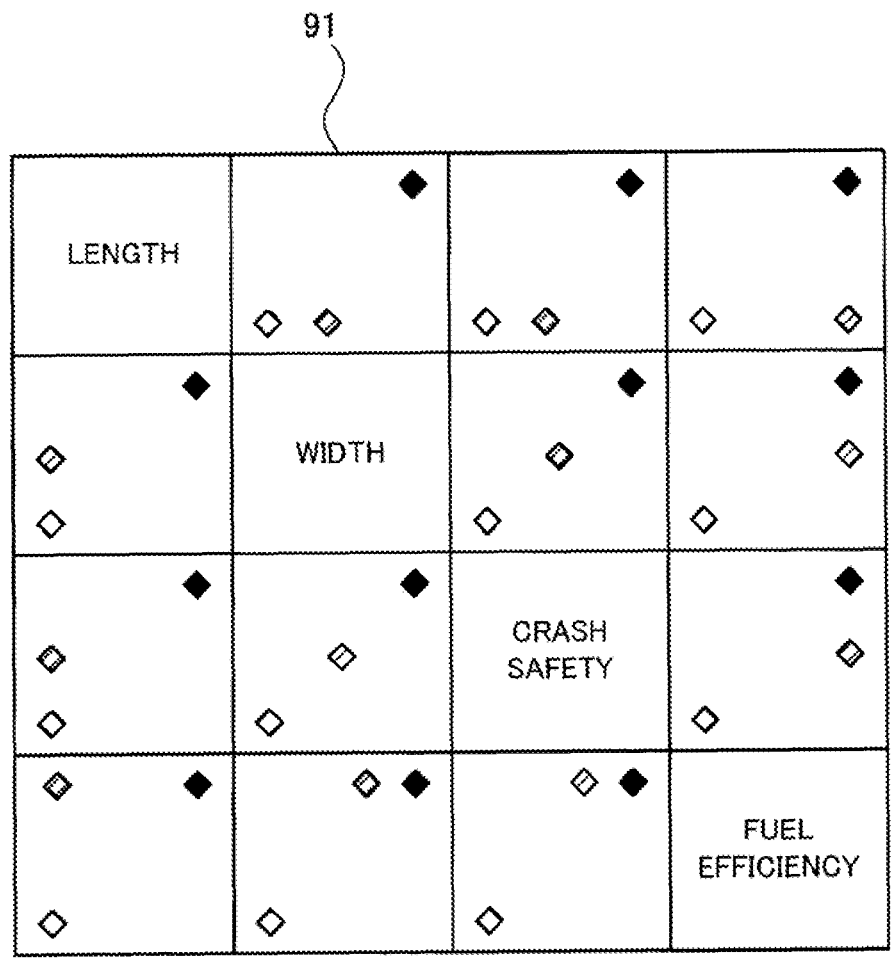
FIG. 6 illustrates a scatter diagram matrix for a comparison example.
Figure 7:
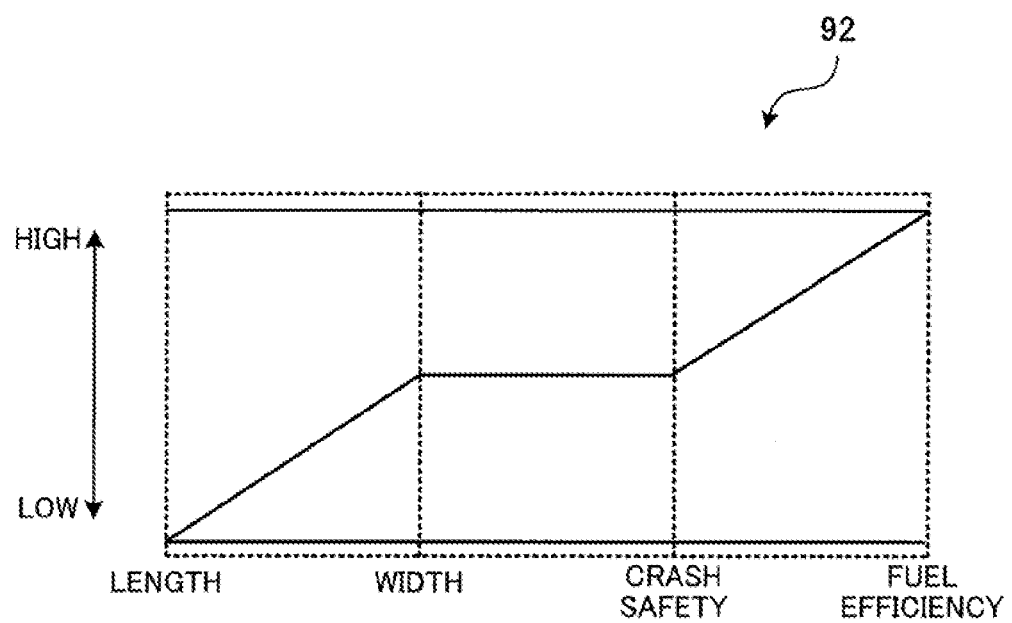
FIG. 7 illustrates a line graph for the comparison example.

FIG. 6 illustrates a scatter diagram matrix for a comparison example, and FIG. 7 illustrates a line graph for the comparison example.

Scatter diagrams 91 in FIG. 6 represent all different combinations of the variables of the data 13a of FIG. 4.

A line graph 92 of FIG. 7 represents all different combinations of the variables of the data 13a of FIG. 4.

The relationships among the input and output variables indicated in the scatter diagrams 17a, 17b, 17c, and 17d enable the user to recognize the results of multi-objective optimization easier compared with the case of analyzing the scatter diagrams 91 and line graph 92. This effect becomes more remarkable as the number of input and output variables increases.

Referring back to FIG. 3, the candidate setting unit 18 accepts a user-specified region of the scatter diagrams 17c and 17d created by the scatter diagram creation unit 17 from a user, and generates the values of the input and output variables and the values of the intermediate variables for regenerating samples that fall within the accepted region. In this case, the scatter diagram creation unit 17 creates scatter diagrams using the values of the input and output variables and the values of the intermediate variables generated by the candidate setting unit 18.

The following describes the operation of the computing apparatus 10.

Figure 8:
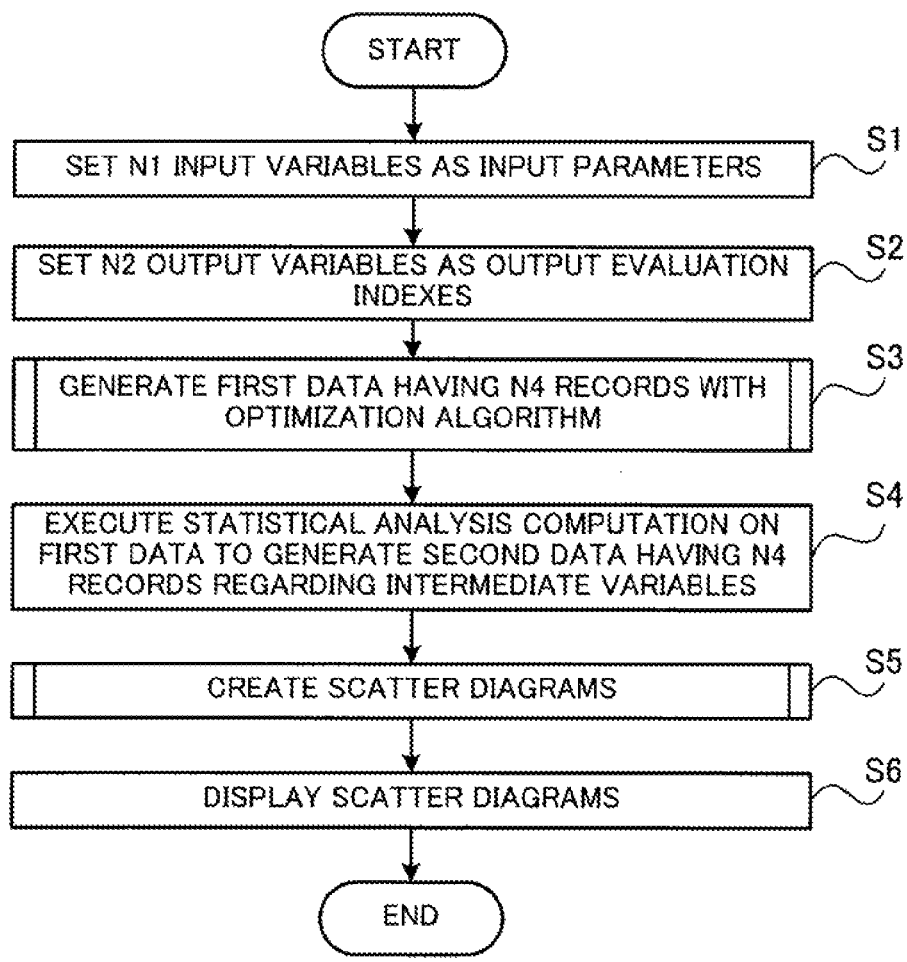
FIG. 8 is a flowchart illustrating an entire process of the computing apparatus.
Figure 9:
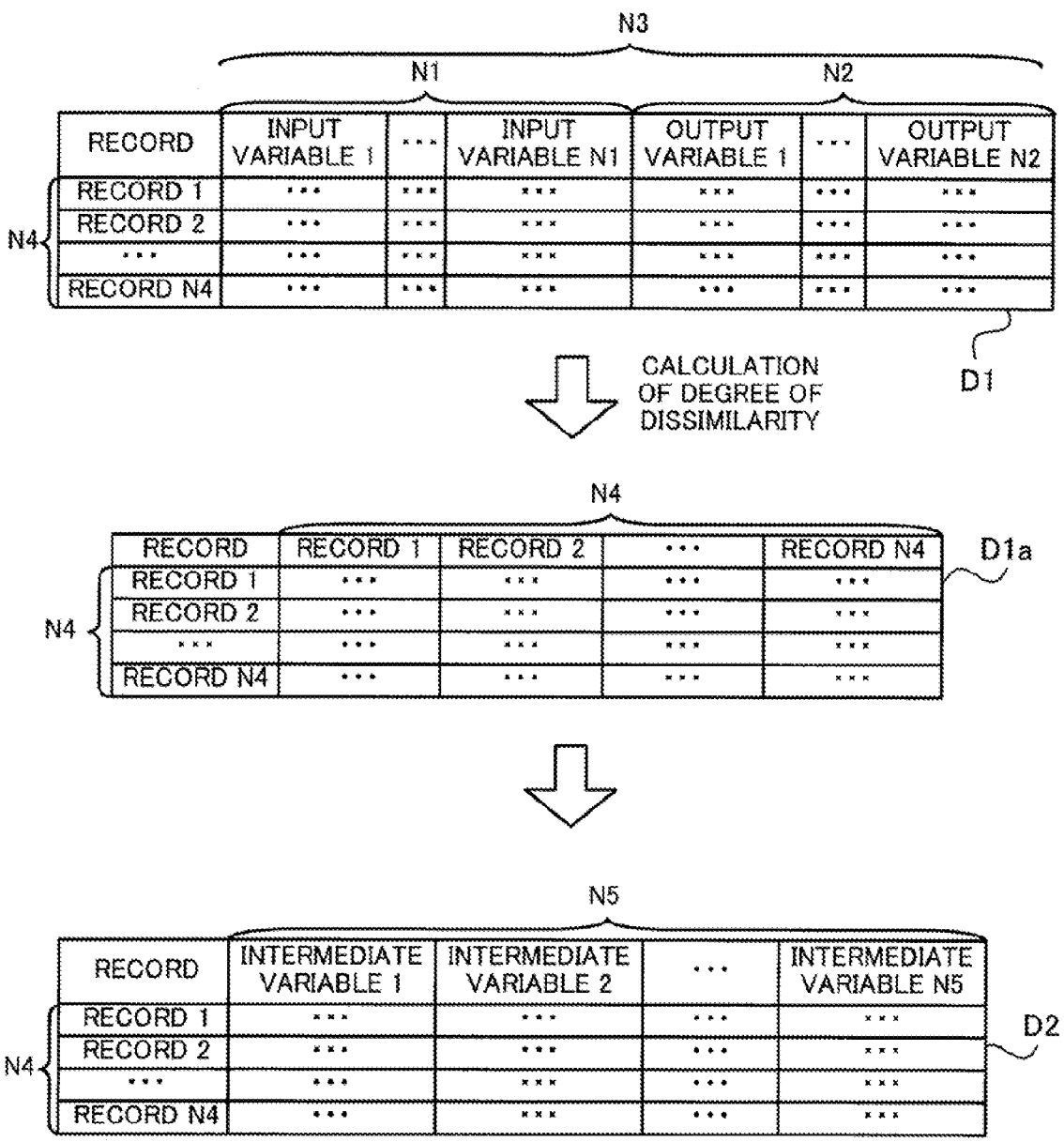
FIG. 9 illustrates an example of data generated through the process of FIG. 8.

FIG. 8 is a flowchart illustrating an entire process of the computing apparatus. FIG. 9 illustrates an example of data generated through the process of FIG. 8.

At step S1, the data generation unit 13 sets N1 input variables stored in the variable storage unit 12 as input parameters. The input parameters are variables regarding inputs to an optimization algorithm. Then, the process proceeds to step S2.

At step S2, the data generation unit 13 sets N2 output variables stored in the variable storage unit 12 as output evaluation indexes. The output evaluation indexes are variables regarding outputs of the optimization algorithm. Then, the process proceeds to step S3.

At step S3, the data generation unit 13 generates first data D1 having N4 records as to the input parameters and output evaluation indexes with the optimization algorithm. The aforementioned data 13a of FIG. 4 is an example of the first data D1. The data generation unit 13 stores the generated first data D1 in the data temporary storage unit 15. Then, the process proceeds to step S4. The process of step S3 will be described in detail later.

At step S4, the statistical analysis computing unit 16 executes statistical analysis computation using Multi-Dimensional Scaling on the first data D1 stored in the data temporary storage unit 15, thereby generating second data D2 having N4 records regarding N5 intermediate variables. More specifically, the statistical analysis computing unit 16 generates data D1a by calculating a degree of dissimilarity from the first data D1. Then, the statistical analysis computing unit 16 generates the second data D2 which defines the two-dimensional coordinate values of each point as the intermediate variables, from the generated data D1a. The statistical analysis computing unit 16 stores the generated second data D2 in the data temporary storage unit 15. Then, the process proceeds to step S5.

At step S5, the scatter diagram creation unit 17 creates scatter diagrams by using the first data D1 and second data D2 stored in the data temporary storage unit 15. Then, the process proceeds to step S6. The scatter diagram creation process will be described in detail later.

At step S6, the scatter diagram creation unit 17 displays the created scatter diagrams on the monitor 104a. Then, the process of FIG. 8 is completed.

Figure 10:
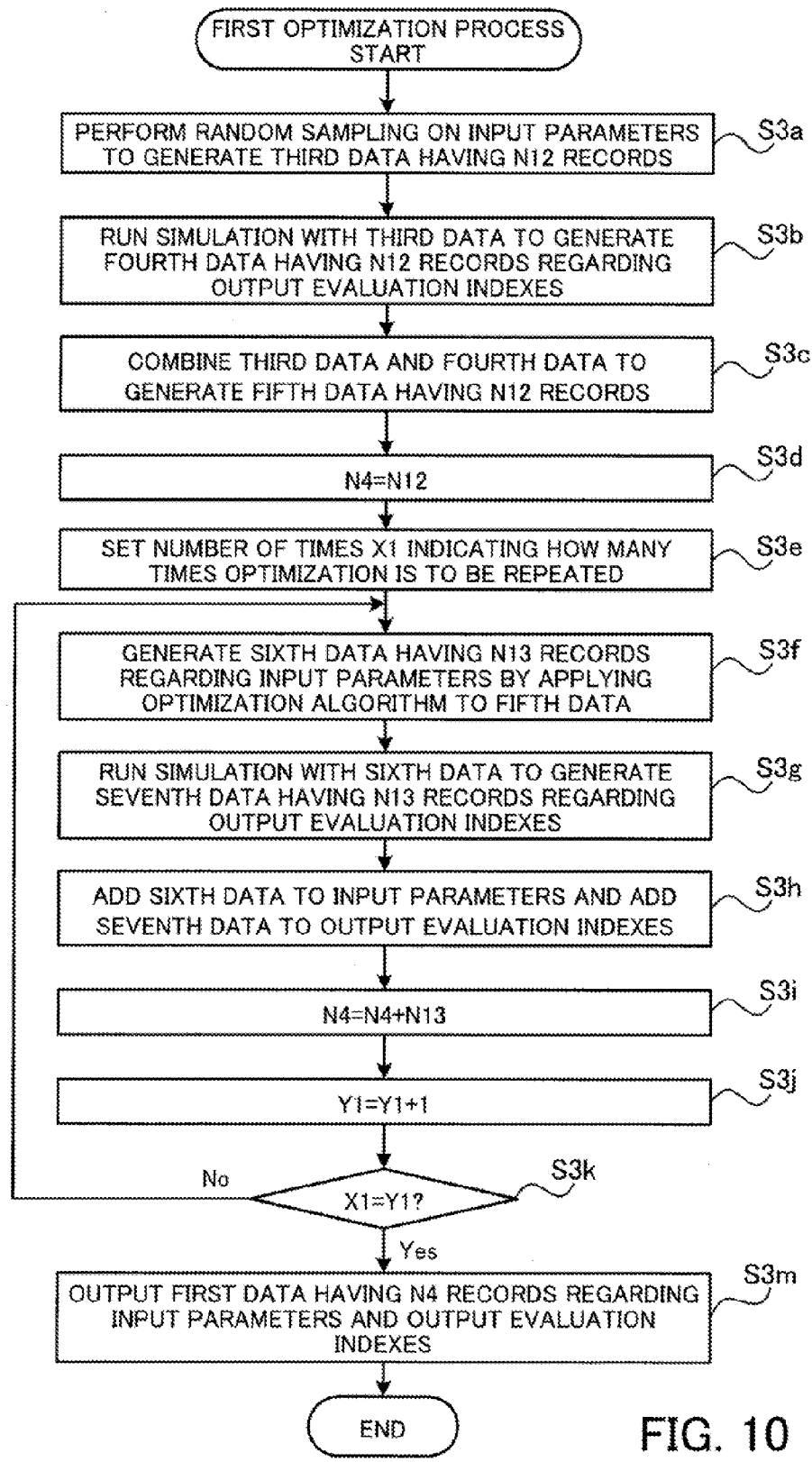
FIG. 10 is a flowchart of a first optimization process.
Figure 11:
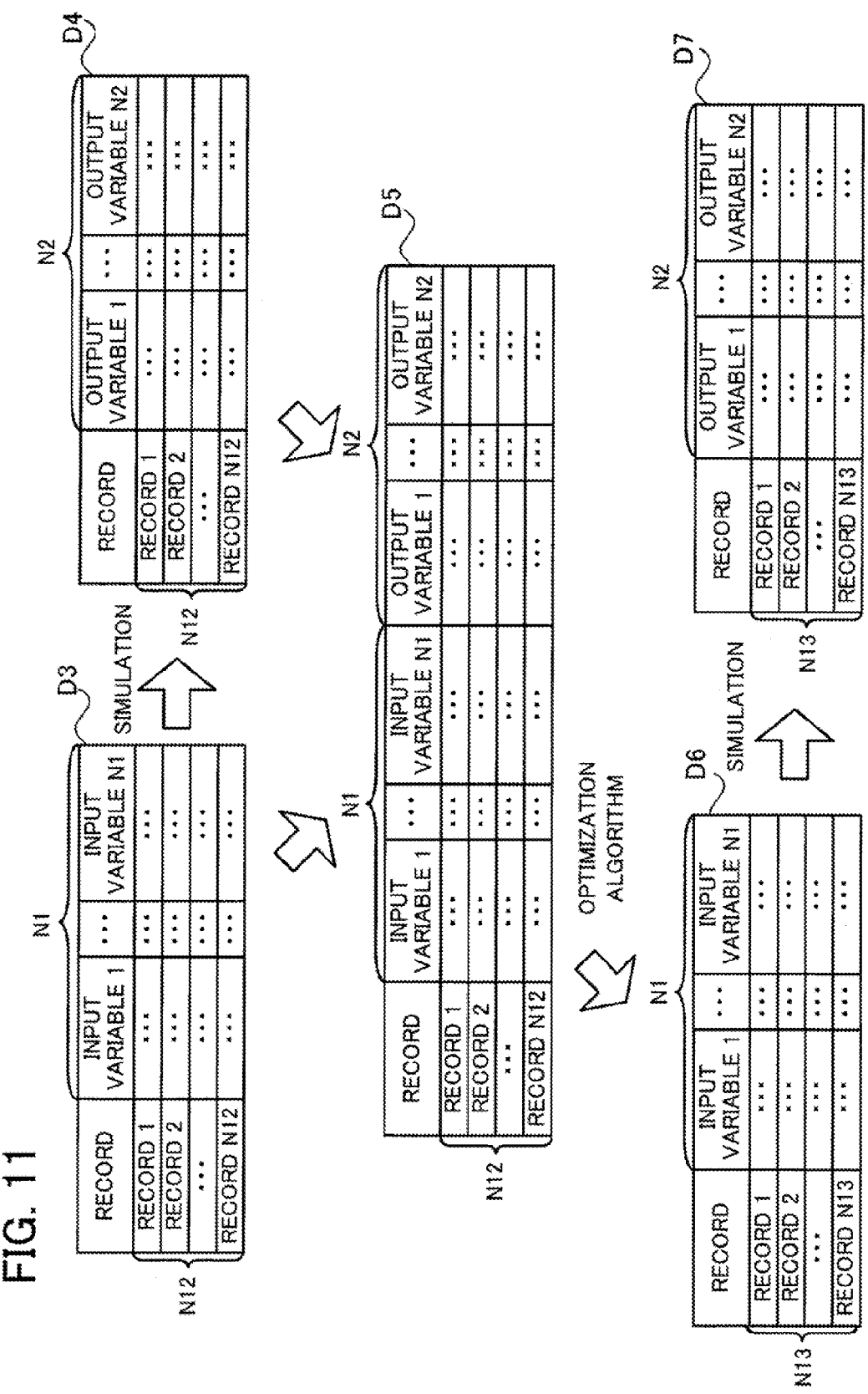
FIG. 11 illustrates an example of data generated through the process of FIG. 10.

The following describes the process (first optimization process) of step S3 of FIG. 8 with reference to FIGS. 10 and 11.

FIG. 10 is a flowchart of a first optimization process. FIG. 11 illustrates an example of data generated through the process of FIG. 10.

At step S3a, the data generation unit 13 generates N12 sample values for the input parameters (N1 input variables) set at step S1 of FIG. 8 with a random sampling method or the like, thereby generating third data D3 having N12 records. Then, the process proceeds to step S3b.

At step S3b, the data generation unit 13 instructs the simulation unit 14 to run a computer simulation with the third data D3 generated at step S3a. The simulation unit 14 runs the computer simulation with the third data D3, thereby generating fourth data D4 having N12 records regarding N2 output evaluation indexes (output variables). The simulation unit 14 returns the generated fourth data D4 to the data generation unit 13.

At step S3c, the data generation unit 13 combines the third data D3 and fourth data D4, thereby generating fifth data D5 having N12 records. Then, the process goes on to step S3d.

At step S3d, the data generation unit 13 substitutes N12 indicating the number of records of the fifth data D5 with N4 indicating the number of records of the first data D1. Then, the process proceeds to step S3e.

At step S3e, the data generation unit 13 sets the number of times X1 indicating how many times the optimization algorithm preset by the user is to be repeated. Then, the process proceeds to step S3f.

At step S3f, the data generation unit 13 generates sixth data D6 having N13 records made up of N1 input parameters that have a high possibility of yielding small output evaluation indexes, by applying the optimization algorithm to the fifth data D5 generated at step S3c. Then, the process proceeds to step S3g.

At step S3g, the data generation unit 13 instructs the simulation unit 14 to run a computer simulation with the sixth data D6 generated at step S3f. The simulation unit 14 runs the computer simulation with the sixth data D6, thereby generating seventh data D7 having N13 records regarding N2 output evaluation indexes. The simulation unit 14 returns the generated seventh data D7 to the data generation unit 13.

At step S3h, the data generation unit 13 adds the sixth data D6 generated at step S3f to the input parameters. In addition, the data generation unit 13 adds the seventh data D7 generated at step S3g to the output evaluation indexes. Then, the process proceeds to step S3i.

At step S3$i$, the data generation unit 13 adds N4 and N13 to be new N4. Then, the process proceeds to step S3$j$.

At step S3$j$, the data generation unit 13 increments the number of times Y1 indicating the number of iterations of the optimization algorithm by one. Then, the process proceeds to step S3$k$.

At step S3$k$, the data generation unit 13 determines whether the number of times Y1 matches the number of times X1. If they match (yes at step S3$k$), the process proceeds to step S3$m$. Otherwise (no at step S3$k$), the process proceeds back to step S3$f$ to repeat step S3$f$ and successive steps.

At step S3$m$, the data generation unit 13 stores the first data D1 having N4 records regarding the input parameters and output evaluation indexes in the data temporary storage unit 15. Then, the process of FIG. 10 is completed.

The following describes a process (scatter diagram creation process) of step S5 of FIG. 8.

Figure 12:
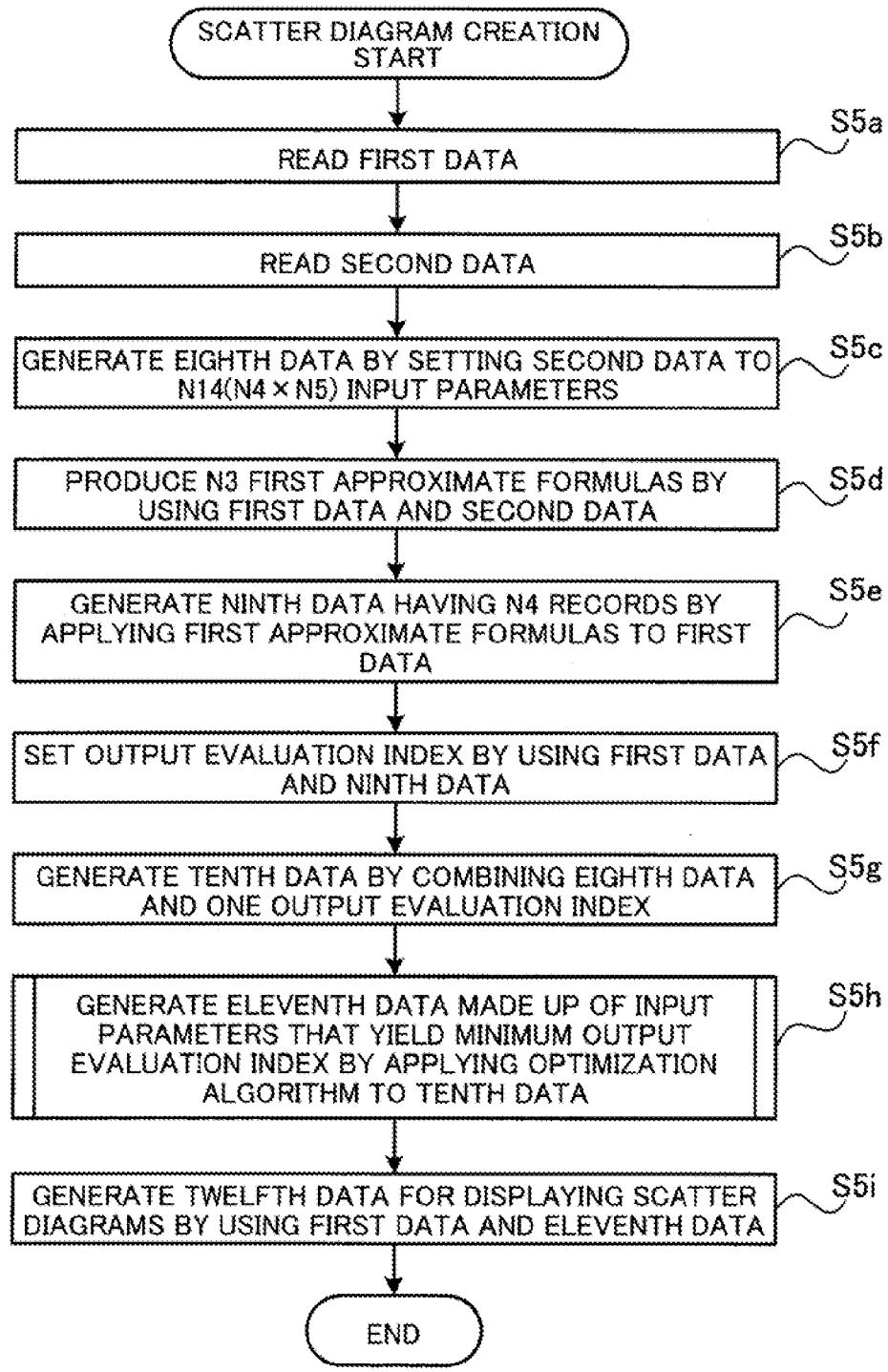
FIG. 12 is a flowchart of a scatter diagram creation process.
Figure 14:
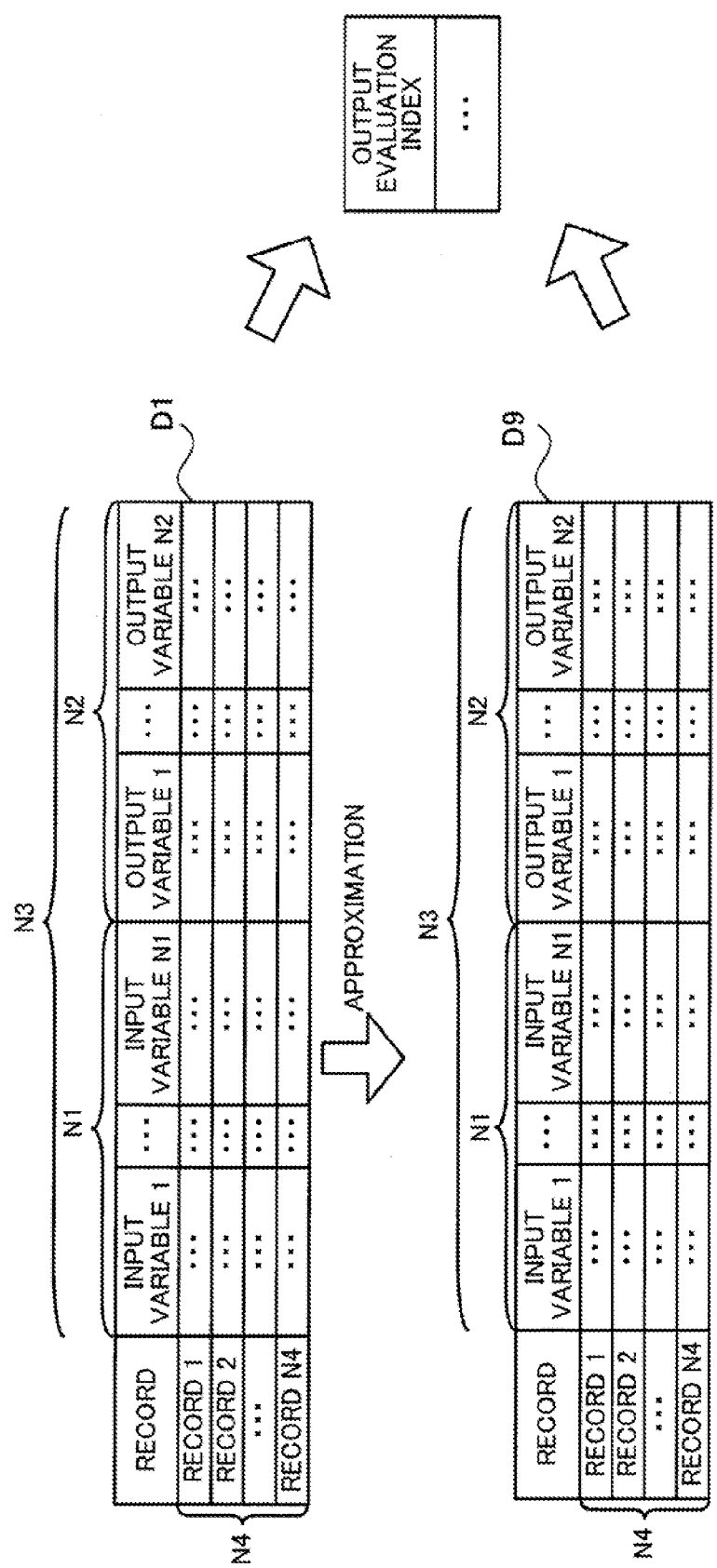
Figure 15:
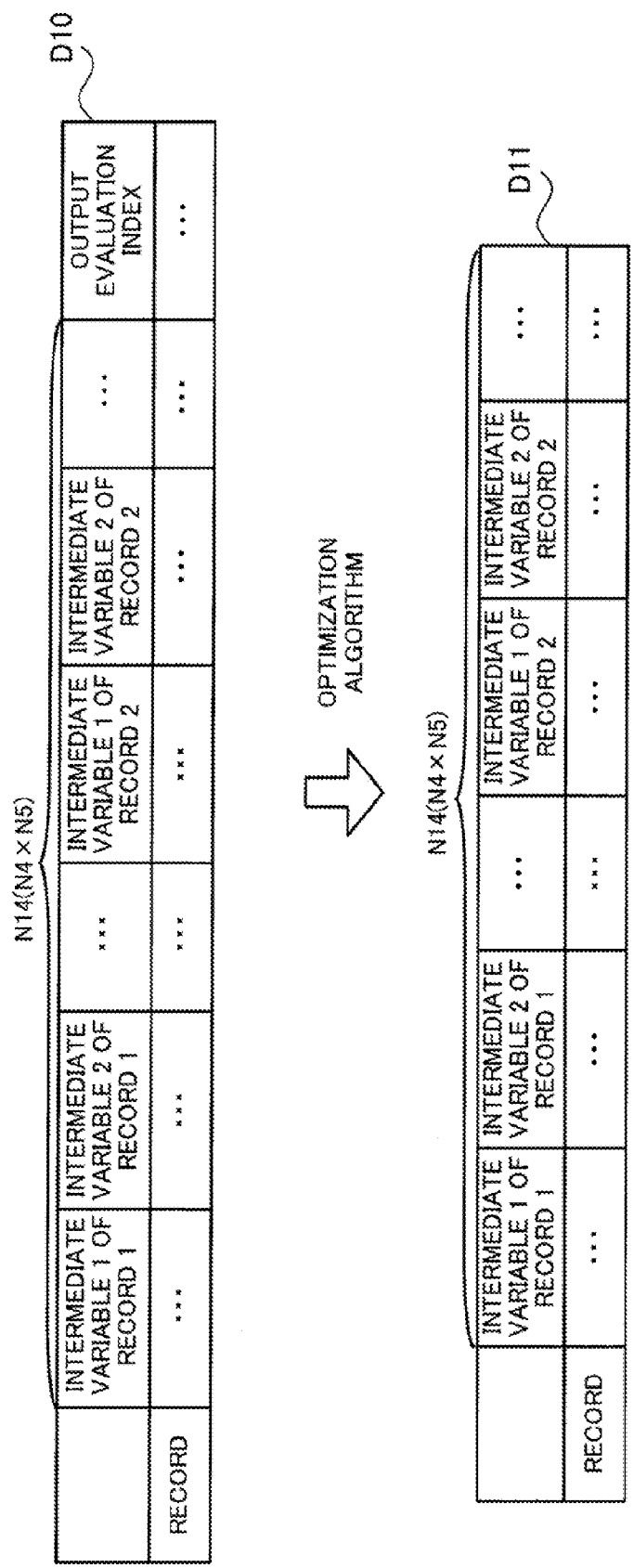

FIG. 12 is a flowchart of a scatter diagram creation process. FIGS. 13 to 16 illustrate an example of data generated through the process of FIG. 12.

At step S5$a$, the scatter diagram creation unit 17 reads the first data D1 from the data temporary storage unit 15. Then, the process proceeds to step S5$b$.

At step S5$b$, the scatter diagram creation unit reads the second data D2 from the data temporary storage unit 15. Then, the process proceeds to step S5$c$.

At step S5$c$, the scatter diagram creation unit 17 generates N14 input parameters. This number of input parameters is a multiplication of the number of records N4 of the first data D1 and the number of intermediate variables N5 of the second data D2. The scatter diagram creation unit 17 then generates eighth data D8 by setting the second data D2 to the generated N14 input parameters. As illustrated in FIG. 13, the eighth data D8 includes N5 pieces of data of the record 1 of the second data D2 arranged in order of the intermediate variable 1 of the record 1, the intermediate variable 2 of the record 1, . . . and then the intermediate variable 1 of the record 2, the intermediate variable 2 of the record 2, . . . and the intermediate variable N5 of the record N4. Then, the process proceeds to step S5$d$.

At step S5$d$, the scatter diagram creation unit produces N3 first approximate formulas for approximating the respective input and output variables of the first data D1 by using the second data D2. In this connection, as a method of producing the approximate formulas, Support Vector Machine (SVM) regression algorithm, Random Forest regression algorithm, or another algorithm may be used. Second, third, and forth approximate formulas, which will be described later, may be produced in the same way as the first approximate formulas. Then, the process proceeds to step S5$e$.

At step S5$e$, the scatter diagram creation unit 17 generates ninth data D9 having N4 records by applying the first approximate formulas produced at step S5$d$ to the first data D1. Then, the process proceeds to step S5$f$.

At step S5$f$, the scatter diagram creation unit 17 obtains one value by calculating a mean square value of differences in input variables and output variables between the first data D1 and the ninth data D9. Then, the scatter diagram creation unit 17 sets the obtained value as an output evaluation index.

At step S5$g$, the scatter diagram creation unit 17 generates tenth data D10 by combining the eighth data D8 generated at step S5$c$ and the one output evaluation index obtained at step S5$f$. Then, the process proceeds to step S5$h$.

At step S5$h$, the scatter diagram creation unit 17 generates eleventh data D11 made up of input parameters that yield the minimum output evaluation index by applying the optimization algorithm to the tenth data D10 generated at step S5$g$. Then, the process proceeds to step S5$i$. The process of this step S5$h$ will be described in detail later.

At step S5$i$, the scatter diagram creation unit generates twelfth data D12 for displaying scatter diagrams by using the first data D1 and the eleventh data D11. More specifically, the scatter diagram creation unit 17 converts the eleventh data D11 into the same format as the second data D2, and generates the twelfth data D12 by combining the obtained data and the first data D1. Then, the process of FIG. 12 is completed.

Figure 16:
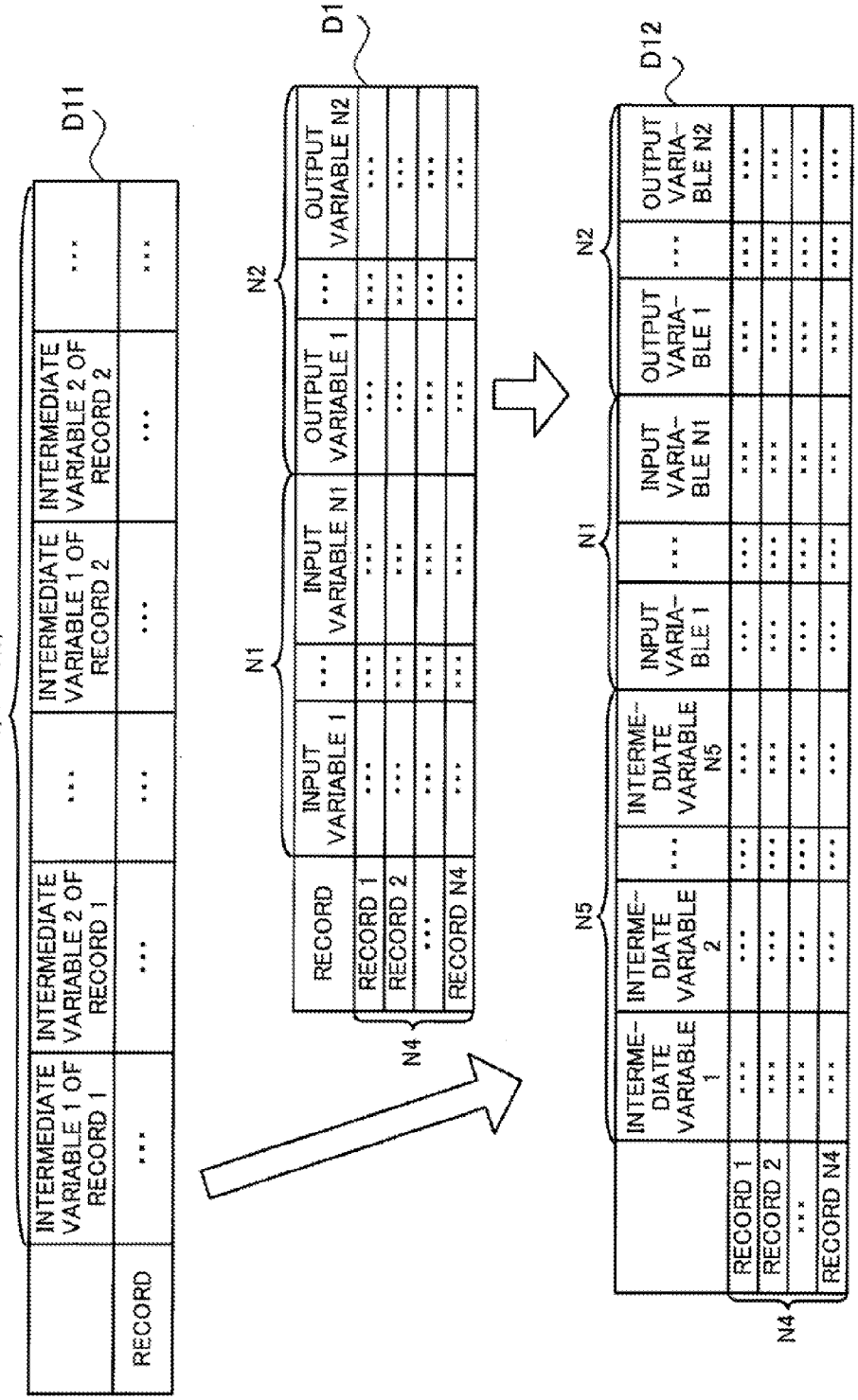

The scatter diagram creation unit 17 is able to create the scatter diagrams 17$a$, 17$b$, 17$c$, and 17$d$, as illustrated in FIG. 5, based on the twelfth data D12 illustrated in FIG. 16. More specifically, the N5 intermediate variables indicate the arrangement positions of the first data D1 in the scatter diagrams. In addition, each data forming the first data D1 arranged at arrangement positions in the scatter diagram is used as a basis for determining colors.

The following describes the process (second optimization process) of step S5$h$ of FIG. 12.

Figure 17:
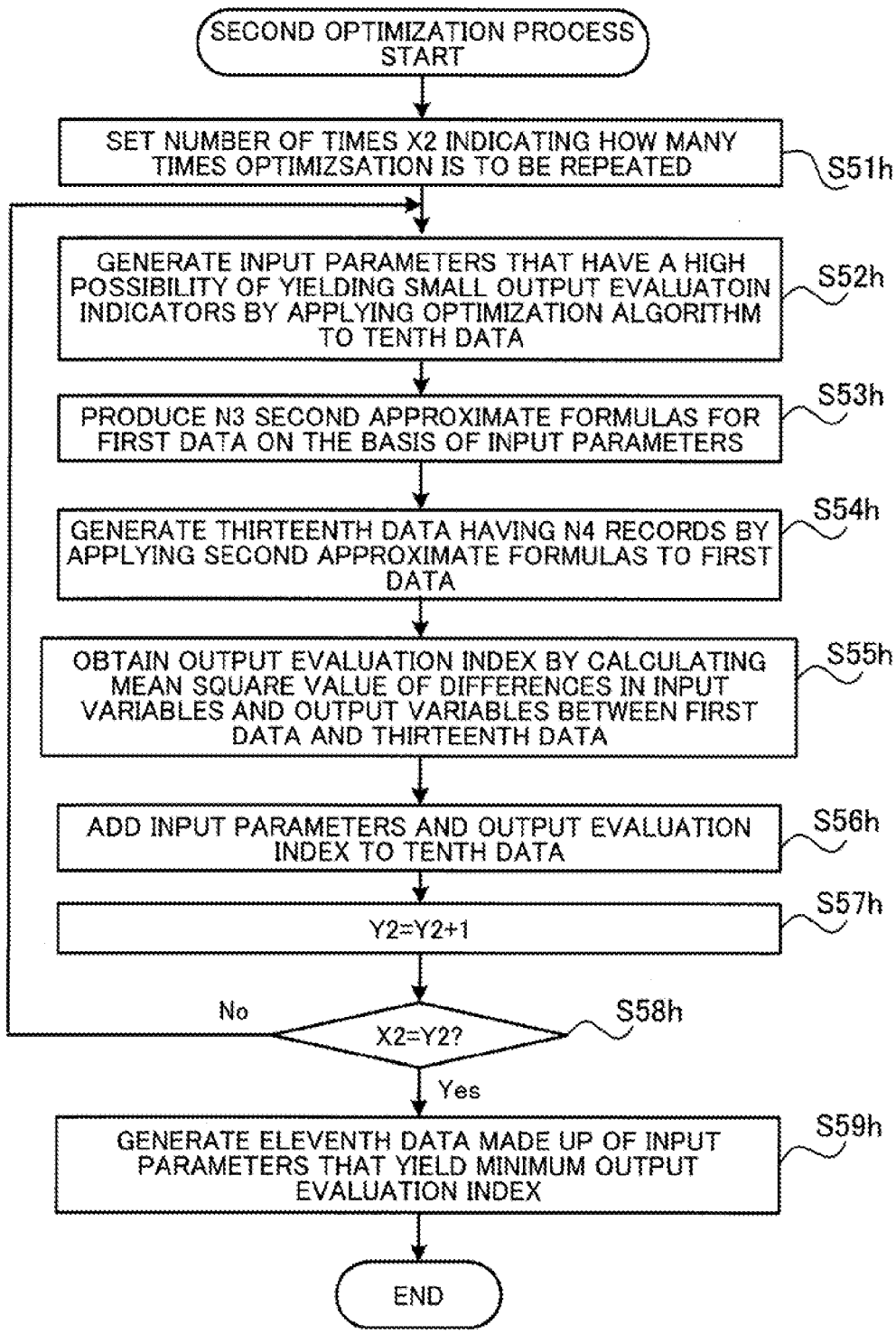
FIG. 17 is a flowchart of a second optimization process.
Figure 18:
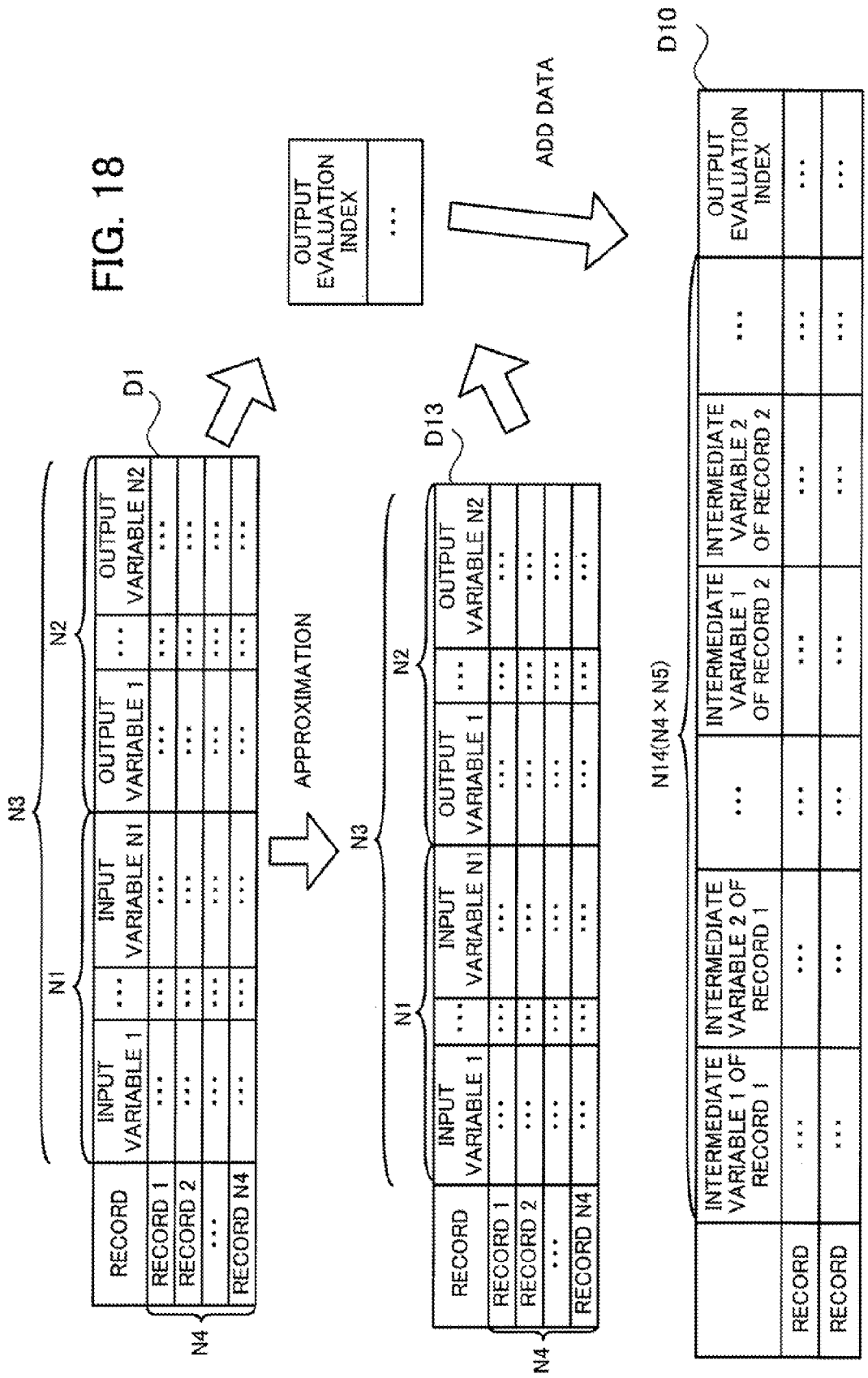
FIG. 18 illustrates an example of data generated through the process of FIG. 17.

FIG. 17 is a flowchart of a second optimization process. FIG. 18 illustrates an example of data generated through the process of FIG. 17.

At step S51$h$, the scatter diagram creation unit 17 sets the number of times X2 indicating how many times the optimization algorithm preset by a user is to be repeated. Then, the process proceeds to step S52$h$.

At step S52$h$, the scatter diagram creation unit generates N14 input parameters that have a high possibility of yielding small output evaluation indexes by applying the optimization algorithm to the tenth data D10 generated at step S5$g$. Then, the process proceeds to step S53$h$.

At step S53$h$, the scatter diagram creation unit produces N3 second approximate formulas for approximating the respective input and output variables of the first data D1 on the basis of the N14 input parameters generated at step S52$h$. Then, the process proceeds to step S54$h$.

At step S54$h$, the scatter diagram creation unit generates thirteenth data D13 having N4 records by applying the second approximate formulas produced at step S53$h$ to the first data D1. Then, the process proceeds to step S55$h$.

At step S55$h$, the scatter diagram creation unit 17 obtains one value by calculating a mean square value of differences in input variables and output variables between the first data D1 and the thirteenth data D13. Then, the scatter diagram creation unit 17 sets the obtained value as an output evaluation index. Then, the process proceeds to step S56$h$.

At step S56$h$, the scatter diagram creation unit adds the N14 input parameters generated at step S52$h$ and the output evaluation index set at step S55$h$ to the tenth data D10.

At step S57$h$, the scatter diagram creation unit 17 increments the number of times Y2 indicating the number of iterations of the optimization algorithm by one. Then, the process proceeds to step S58$h$.

At step S58$h$, the scatter diagram creation unit 17 determines whether the number of times Y2 matches the number of times X2. If they match (yes at step S58$h$), the process proceeds to step S59$h$. Otherwise (no at step S58$h$), the process proceeds back to step S52$h$ to repeat step S52$h$ and subsequent steps.

At step S59$h$, the scatter diagram creation unit 17 generates eleventh data D11 made up of input parameters that yield the minimum output evaluation index, out of the tenth data D10. Then, the process of FIG. 17 is completed.

As described above, the computing apparatus 10 creates and displays the scatter diagrams 17$a$, 17$b$, 17$c$, and 17$d$ even if there are many input variables and many output variables, which enables a user to easily understand the results of multi-objective optimization.

By the way, by specifying a desired range of output values in the scatter diagrams 17a, 17b, 17c, and 17d, and causing the computing apparatus 10 to run a computer simulation within the specified range, the user is able to recognize a more detailed tendency of data for the specified range.

Figure 19:
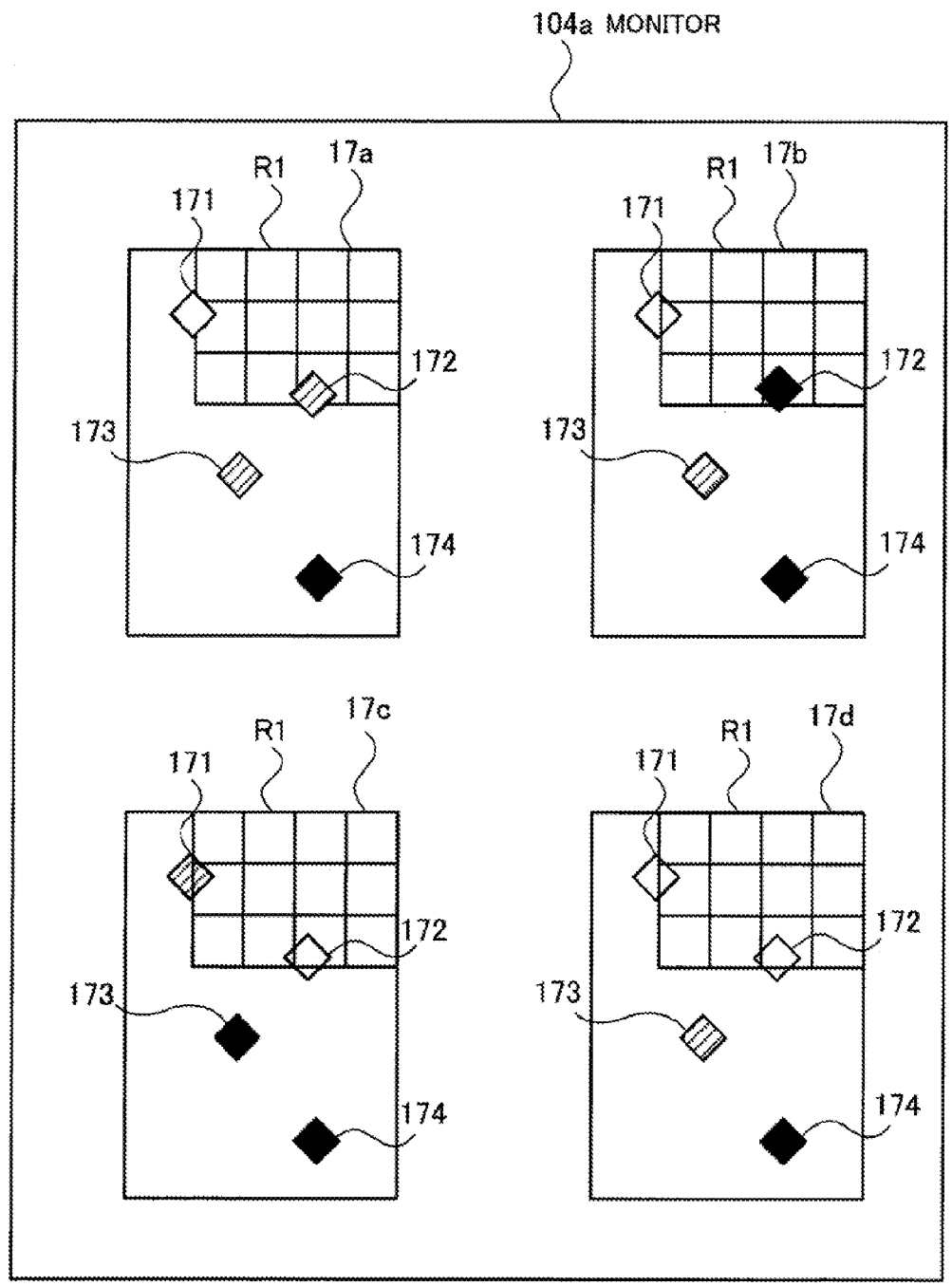
FIG. 19 illustrates an example of a range specification.

FIG. 19 illustrates one example of a range specification.

A range R1 is specified by the user since samples 171 and 172 in the upper right side of the scatter diagram 17d indicate good fuel efficiency.

The candidate setting unit 18 produces approximate formulas for predicting data of input variables, on the basis of the arrangement of the candidate samples, and then, calculates the data of the input variables by applying the produced approximate formulas to the candidate samples. Then, the candidate setting unit 18 instructs the simulation unit 14 to run a computer simulation with the calculated data of the input variables. The simulation unit 14 runs the computer simulation with the data of the input variables, thereby generating the data of the output variables corresponding to the input variables. The simulation unit 14 returns the generated data of the output variables to the candidate setting unit 18. The candidate setting unit 18 supplies the scatter diagram creation unit 17 with data including the generated input variables and output variables and intermediate variables indicating the arrangement positions of the candidate samples. The scatter diagram creation unit 17 creates scatter diagrams based on the received data. As a result, scatter diagrams for the candidate samples are obtained.

The candidate setting unit 18 produces approximate formulas for predicating data of input variables, on the basis of the arrangement of the candidate samples, and then, calculates the data of the input variables by applying the produced approximate formulas to the candidate samples. Then, the candidate setting unit 18 instructs the simulation unit 14 to run a computer simulation with the calculated data of the input variables. The simulation unit 14 runs the computer simulation with the data of the input variables, thereby generating the data of the output variables corresponding to the input variables. The simulation unit 14 returns the generated data of the output variables to the candidate setting unit 18. The candidate setting unit 18 supplies the scatter diagram creation unit 17 with data including the generated input variables and output variables and intermediate variables indicating the arrangement positions of the candidate samples. The scatter diagram creation unit 17 creates scatter diagrams based on the received data. As a result, scatter diagrams for the candidate samples are obtained.

The following describes the operation of the candidate setting unit 18.

Figure 20:
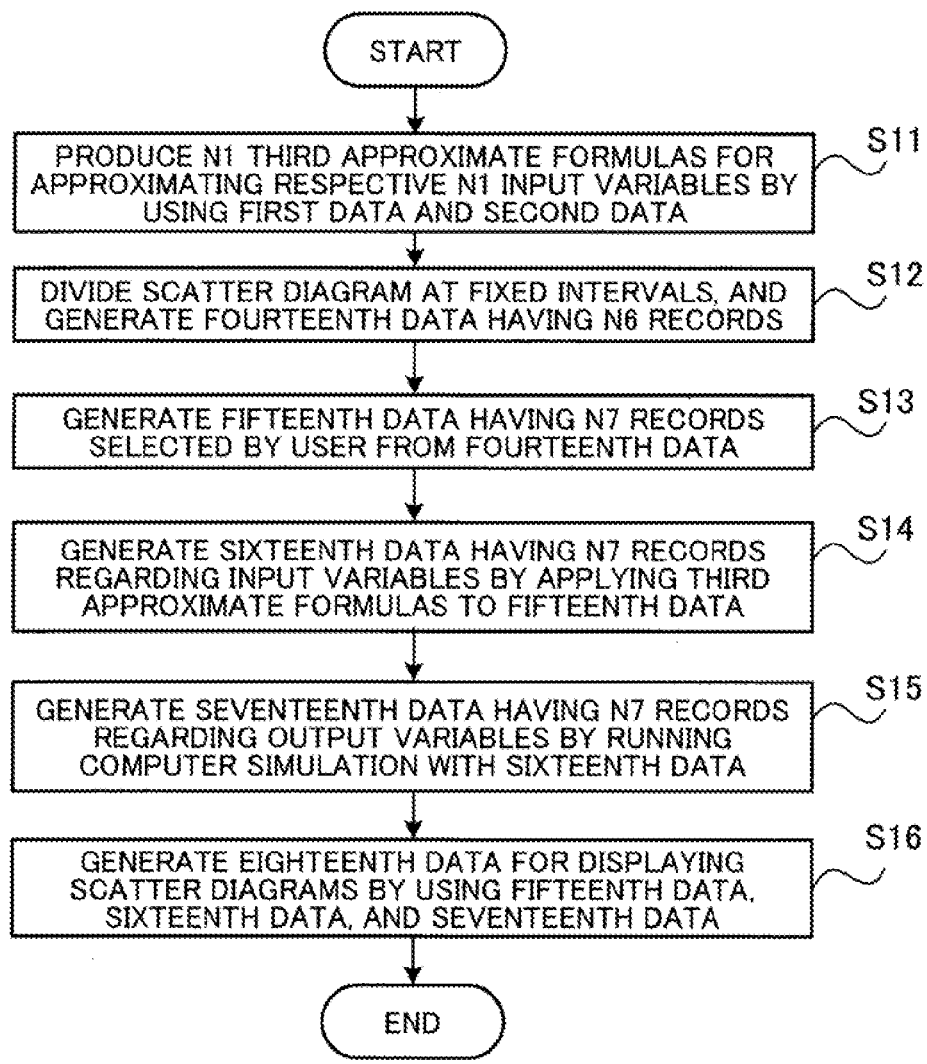
FIG. 20 is a flowchart of a candidate setting process.
Figure 21:
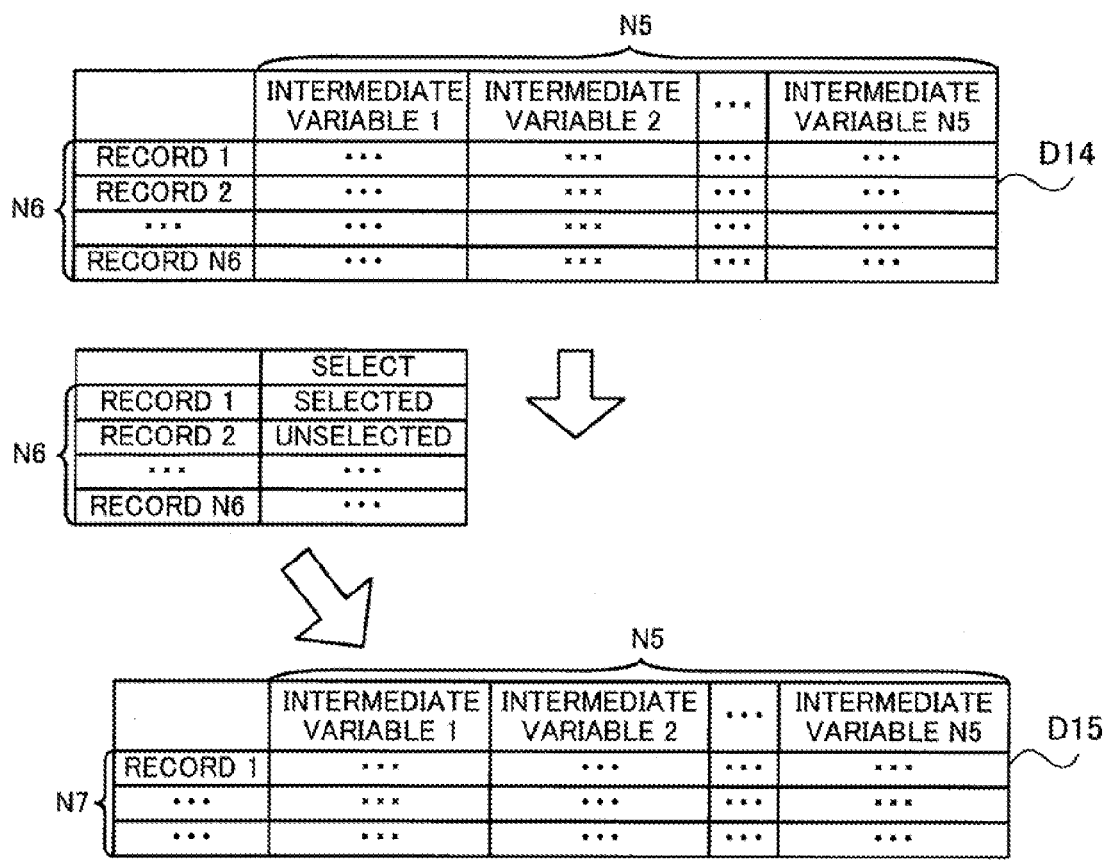
FIGS. 21 and 22 illustrate an example of data generated through the process of FIG. 20.
Figure 22:
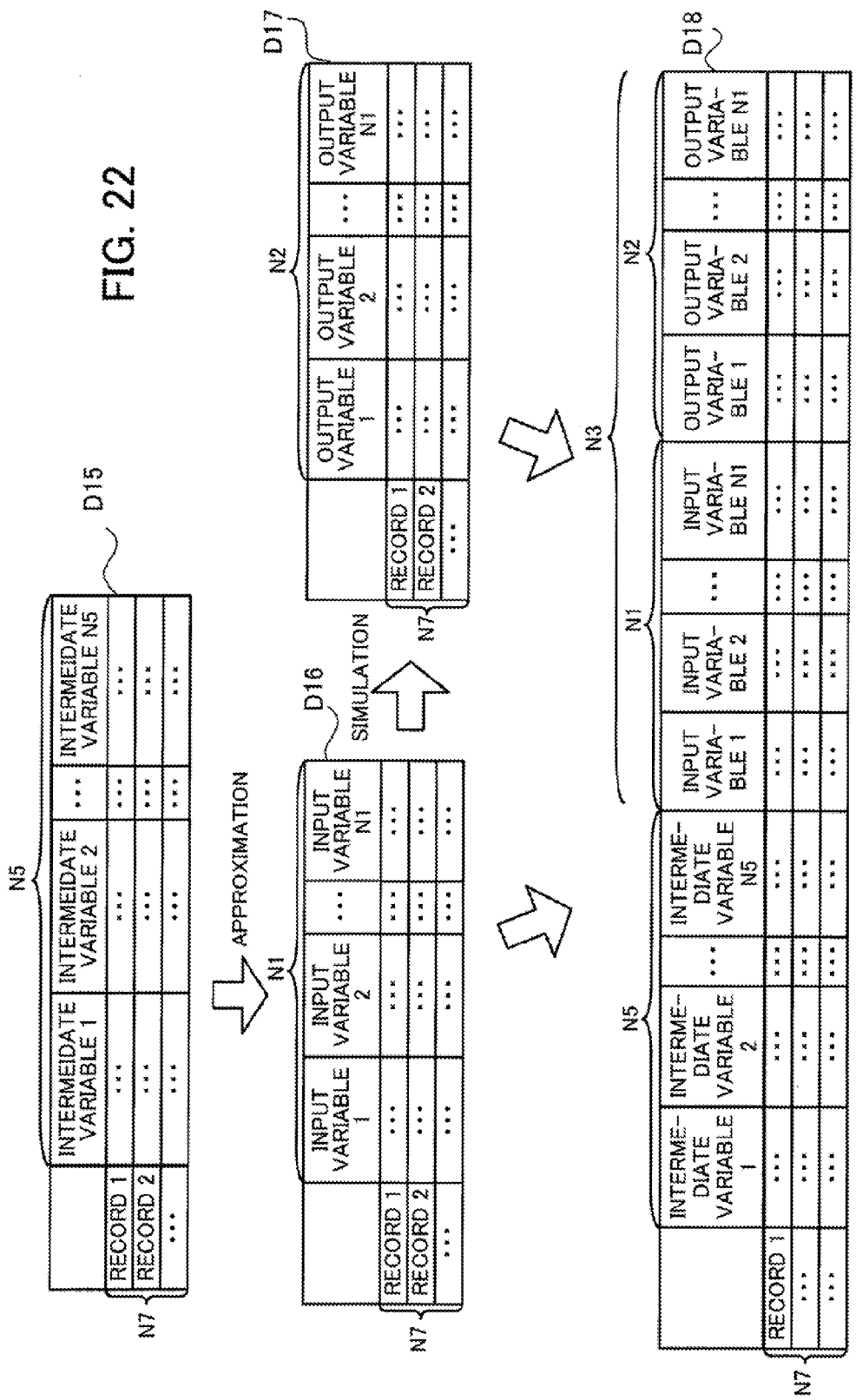

FIG. 20 is a flowchart illustrating the process of the candidate setting unit. FIGS. 21 and 22 illustrate an example of data generated through the process of FIG. 20.

At step S11, the candidate setting unit 18 produces N1 third approximate formulas for approximating the respective input variables of the twelfth data D12 by using the first data D1 and second data D2. Then, the process proceeds to step S12.

At step S12, the candidate setting unit 18 divides a scatter diagram created by the scatter diagram creation unit 17 at fixed intervals, and sets coordinates at each intersection point of grids. Then, the candidate setting unit 18 sets the number of dimensions of the set coordinates (for example, two, i.e., X coordinate and Y coordinate, in the scatter diagram 17a) as intermediate variables, and generates fourteenth data D14 having N6 records with the coordinate values as the values of the records. Then, the process proceeds to step S13.

At step S13, the candidate setting unit 18 generates fifteenth data D15 having N7 records obtained by extracting the coordinate values within a range selected by the user, out of the fourteenth data D14 generated at step S12. Then, the process proceeds to step S14.

At step S14, the candidate setting unit 18 generates sixteenth data D16 having N7 records regarding the input variables by applying the third approximate formulas to the fifteenth data D15. Then, the process proceeds to step S15.

At step S15, the candidate setting unit 18 instructs the simulation unit 14 to run a computer simulation with the sixteenth data D16 generated at step S14. The simulation unit 14 runs the computer simulation with the sixteenth data D16, thereby generating seventeenth data D17 having N7 records regarding the output variables. The simulation unit 14 returns the generated seventeenth data D17 to the candidate setting unit 18.

At step S16, the candidate setting unit 18 generates eighteenth data D18 for displaying scatter diagrams by combining the fifteenth data D15, sixteenth data D16, and seventeenth data D17. Now, the process of the candidate setting unit 18 is completed.

The scatter diagram creation unit 17 creates scatter diagrams based on the eighteenth data D18 generated by the candidate setting unit 18.

This candidate setting unit 18 produces the third approximate formulas for approximating values of the respective input variables on the basis of the arrangement of the multi-dimensional scaling, and then calculates the values of the input variables by applying the produced approximate formulas to the candidate samples. Then, the computer simulation is run for the calculated input variables in order to obtain output variables. Therefore, even in the case where many variables need to be displayed in scatter diagrams, the number of variables may be decreased while maintaining the positional relationship of data among the scatter diagrams, which enables the user to more easily recognize the results of multi-objective optimization.

This embodiment selects candidate samples by dividing a scatter diagram at fixed intervals. Alternatively, Voronoi tessellation may be used as a method for selecting candidate samples. The Voronoi tessellation is a method of drawing a perpendicular bisector of a line connecting adjacent coordinates to thereby partition the nearest neighbor area of each coordinates.

(C) Third Embodiment

The following describes a computing apparatus according to a third embodiment.

The following mainly describes differential features of the computing apparatus of the third embodiment from the computing apparatus of the second embodiment, and description on the same features will not be repeated.

In a computing apparatus according to the third embodiment, a candidate setting unit 18 has a different function from that of the computing apparatus of the second embodiment.

The candidate setting unit 18 of the third embodiment sets candidate samples at fixed intervals in an entire scatter diagram, without receiving specification of a region R1 from a user.

Figure 23:
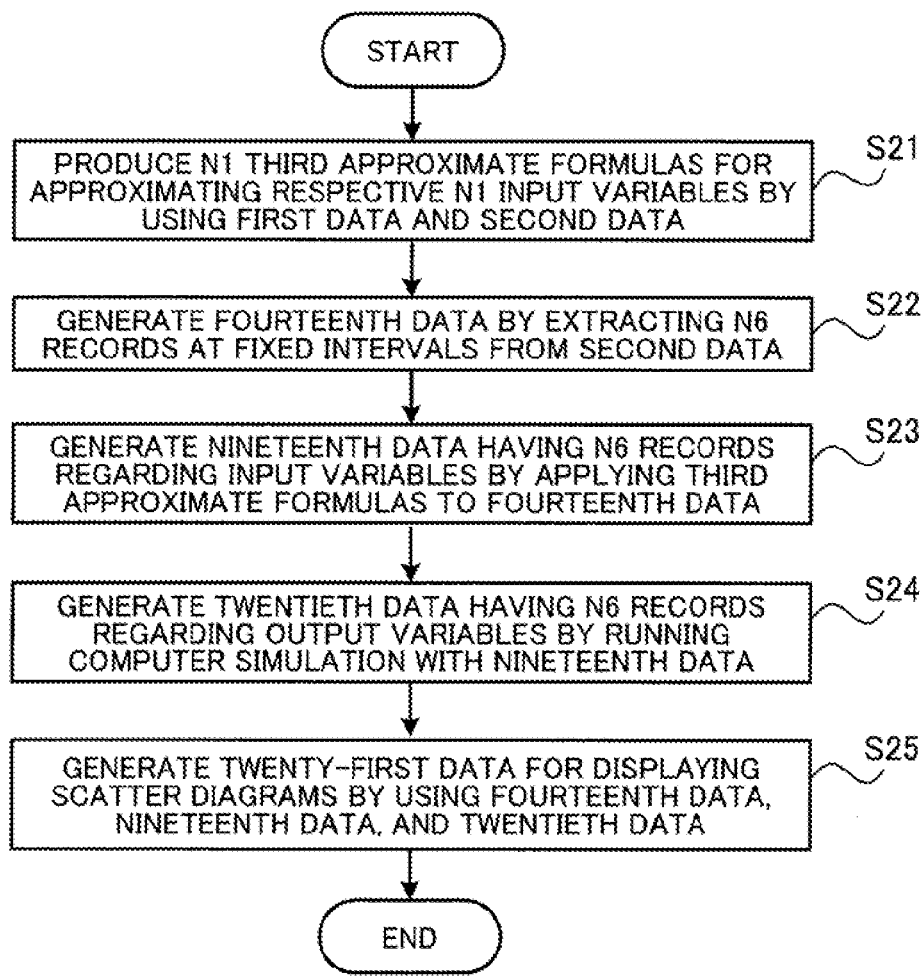
FIG. 23 is a flowchart illustrating a process of a candidate setting unit according to a third embodiment.
Figure 24:
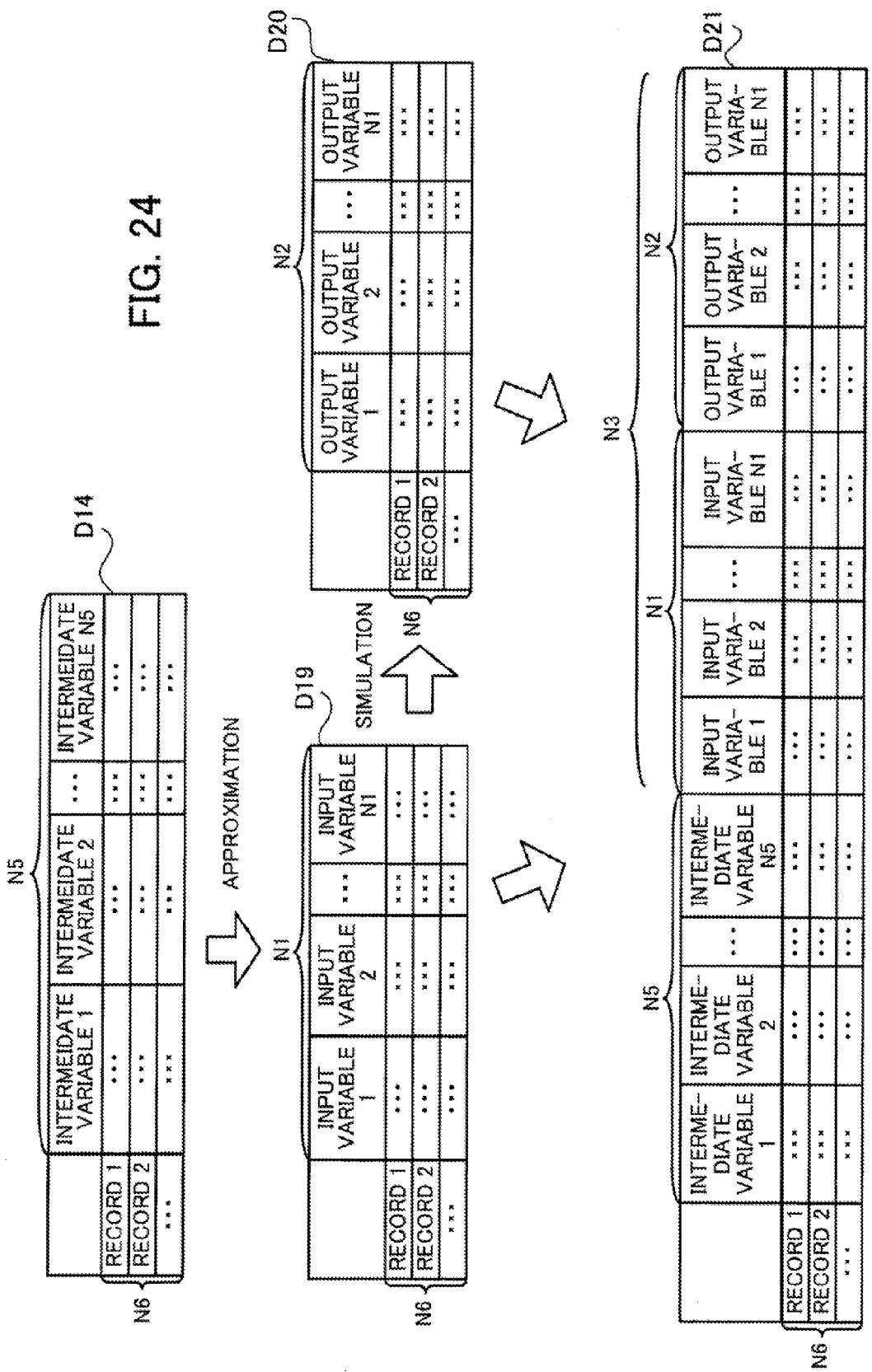
FIG. 24 illustrates an example of data generated through the process of FIG. 23.

FIG. 23 is a flowchart of a process performed by a candidate setting unit according to the third embodiment. FIG. 24 illustrates an example of data generated through the process of FIG. 23.

At step S21, the candidate setting unit 18 produces third approximate formulas in the same way as step S11 of FIG. 20. Then, the process proceeds to step S22.

At step S22, the candidate setting unit 18 generates fourteenth data D14 in the same way as step S12 of FIG. 20. Then, the process proceeds to step S23.

At step S23, the candidate setting unit 18 generates nineteenth data D19 having N6 records regarding input variables by applying the third approximate formulas to the fourteenth data D14. Then, the process proceeds to step S24.

At step S24, the candidate setting unit 18 instructs the simulation unit 14 to run a computer simulation with the nineteenth data D19 generated at step S23. The simulation unit 14 runs the computer simulation with the nineteenth data D19, thereby generating twentieth data D20 having N6 records regarding output variables. The simulation unit 14 returns the generated twentieth data D20 to the candidate setting unit 18.

At step S25, the candidate setting unit 18 generates twenty-first data D21 for displaying scatter diagrams by combining the fourteenth data D14, nineteenth data D19, and twentieth data D20. Then, the process of the candidate setting unit 18 is completed.

The candidate setting unit 18 according to the third embodiment is also capable of reducing the number of variables even if there are many variables to be displayed in scatter diagrams, which enables the user to more easily understand the results of multi-objective optimization.

(D) Fourth Embodiment

The following describes a computing apparatus according to a fourth embodiment.

The following mainly describes differential features of the computing apparatus of the fourth embodiment from the computing apparatus of the third embodiment, and description on the same features will not be repeated.

In a computing apparatus according to the fourth embodiment, a candidate setting unit has a different function from that of the computing apparatus of the third embodiment.

A candidate setting unit 18 according to the fourth embodiment selects records with good values of output variables by using the values of the intermediate variables included in the fourteenth data D14.

The following describes the operations of the candidate setting unit 18 and scatter diagram creation unit 17 of the fourth embodiment with reference to a flowchart.

Figure 25:
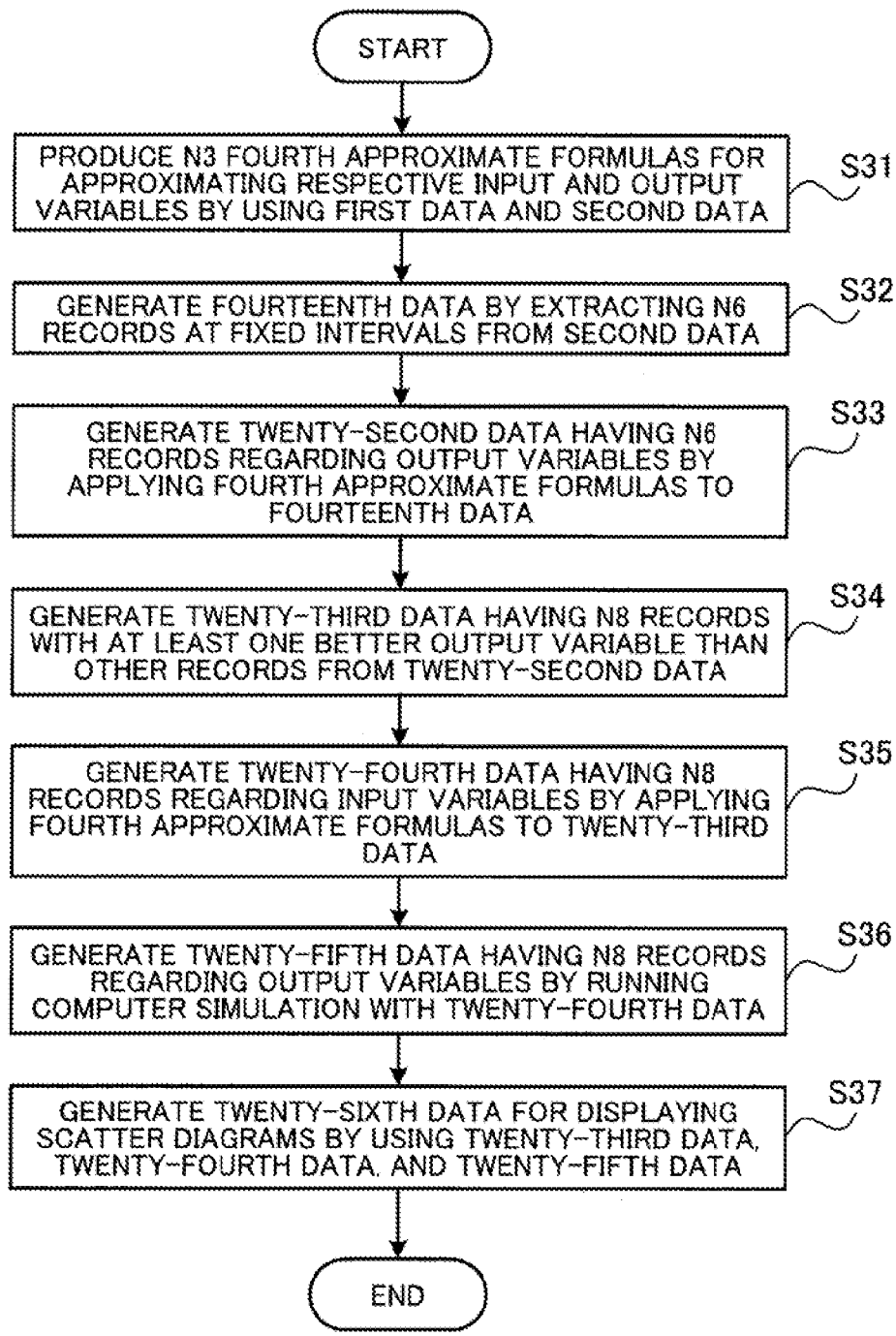
FIG. 25 is a flowchart illustrating a process of a candidate setting unit according to a fourth embodiment.
Figure 26:
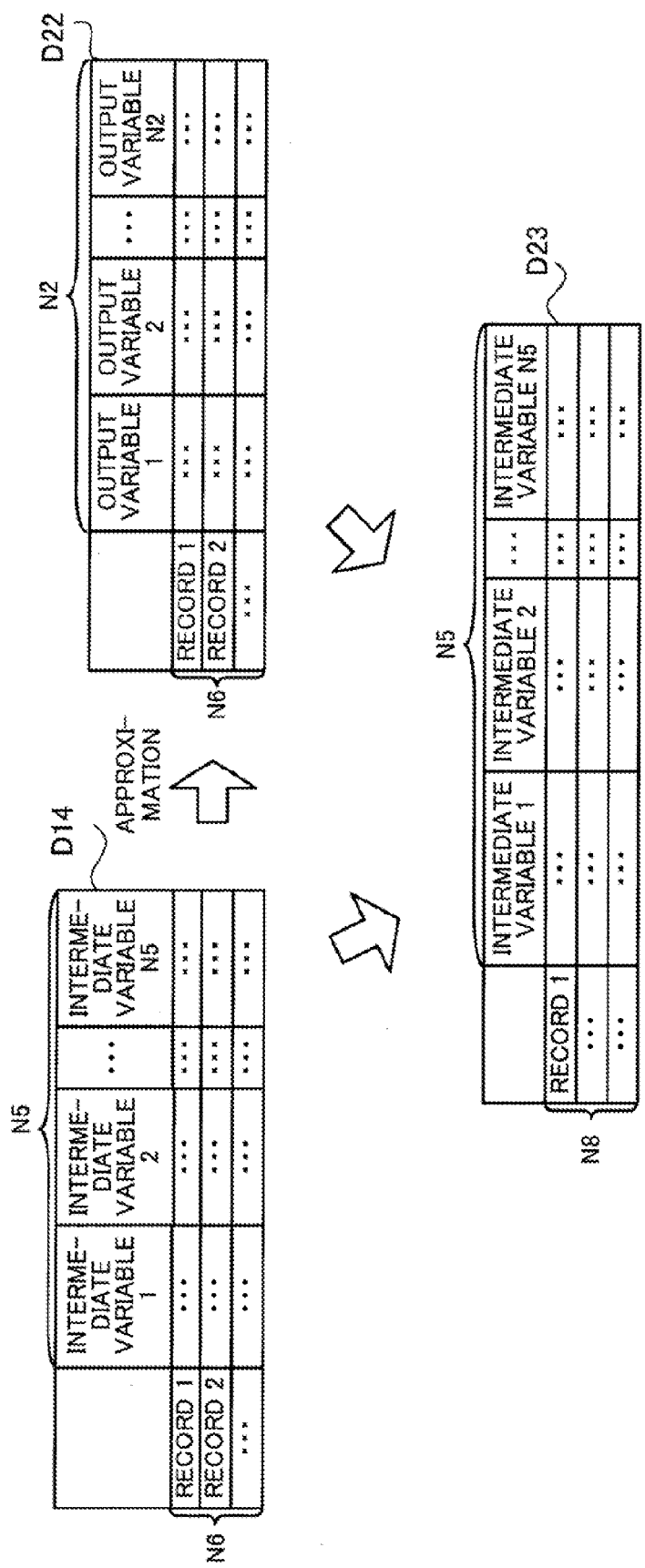
FIGS. 26 and 27 illustrate an example of data generated through the process of FIG. 25.
Figure 27:
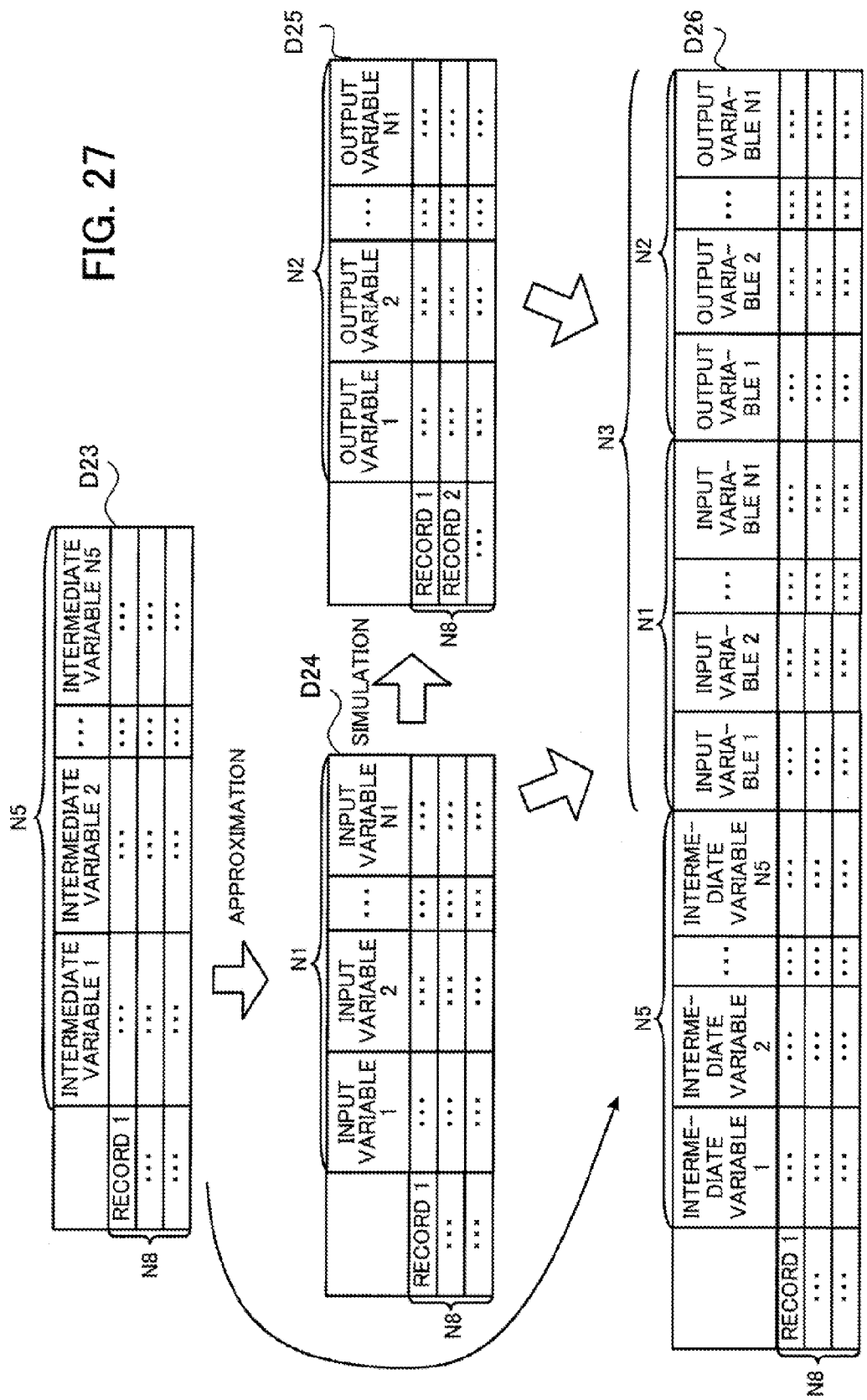

FIG. 25 is a flowchart illustrating the process of the candidate setting unit according to the fourth embodiment. FIGS. 26 and 27 illustrate an example of data generated through the process of FIG. 25.

At step S31, the candidate setting unit 18 produces N3 fourth approximate formulas for approximating the respective input and output variables included in the twelfth data D12 by using the first data D1 and second data D2. Then, the process proceeds to step S32.

At step S32, the candidate setting unit 18 generates fourteenth data D14 in the same way as step S12 of FIG. 20. Then, the process proceeds to step S33.

At step S33, the candidate setting unit 18 generates twenty-second data D22 having N6 records regarding the output variables by applying the fourth approximate formulas produced at step S31 to the fourteenth data D14. Then, the process proceeds to step S34.

At step S34, the candidate setting unit 18 selects records with at least one good output variable out of the values of the records included in the twenty-second data D22. Then, the candidate setting unit 18 generates twenty-third data D23 having N8 records regarding the intermediate variables corresponding to the selected records. Then, the process proceeds to step S35. The following describes a specific example of this step S34.

Figure 28:
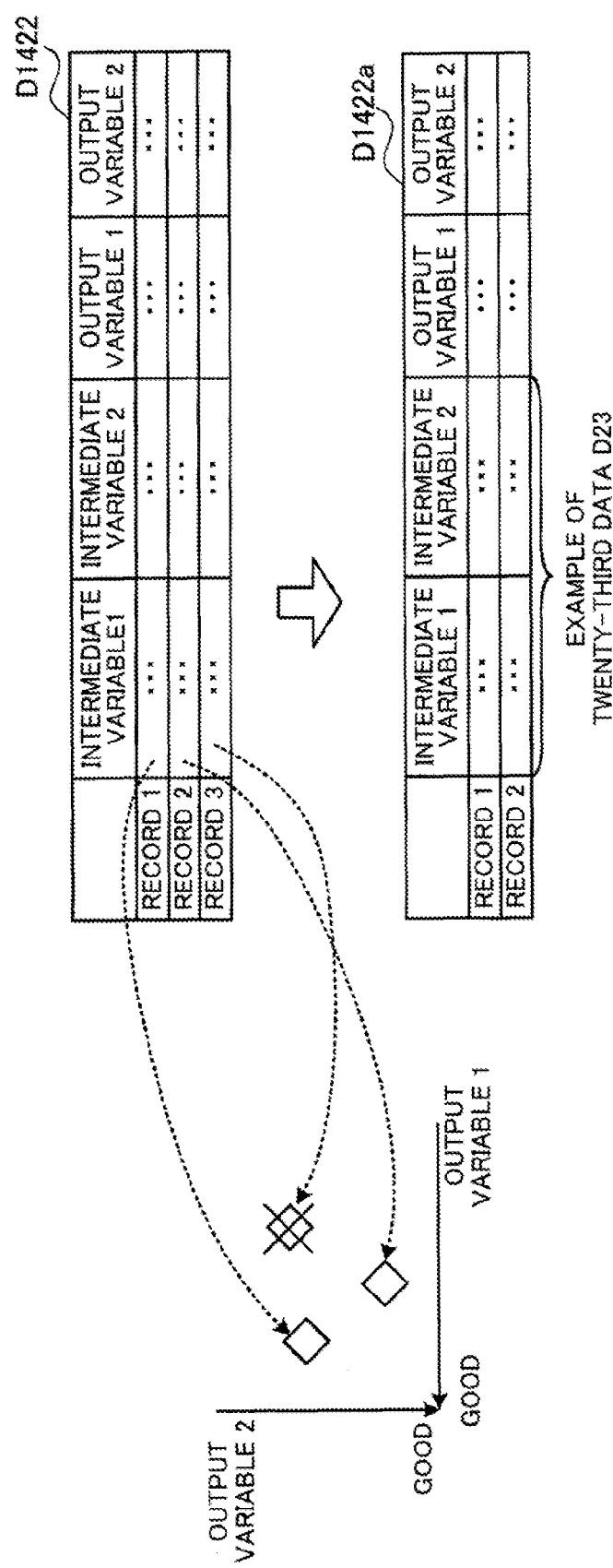
FIG. 28 is a diagram explaining a process of the candidate setting unit according to the fourth embodiment.

FIG. 28 is a diagram explaining the process of the candidate setting unit of the fourth embodiment.

Data D1422 illustrated in FIG. 28 is one example of data obtained by combining the fourteenth data D14 and twenty-second data D22. The data D1422 has three records regarding two intermediate variables and two output variables.

The candidate setting unit 18 selects data including records each with at least a value of one output variable better than that of the other records, with reference to the records regarding the output variables included in the data D1422. Now assume that preferable records in the data D1422 are that the output variable 1 and output variable 2 have smaller values.

The candidate setting unit 18 according to the fourth embodiment creates a graph with a horizontal axis representing values of the output variable 1 and a vertical axis representing values of the output variable 2. Then, the candidate setting unit 18 plots the values of the intermediate variable 1 of the records 1 to 3 included in the data D1422 on the created graph. The candidate setting unit 18 then sets a record that does not have a good value as compared with the other records, as a record to be deleted.

As illustrated in FIG. 28, with respect to the output variable 1, the value of the record 1 is better than the values of the records 2 and 3. Therefore, the candidate setting unit 18 keeps the record 1. With respect to the output variable 2, the value of the record 2 is better than the values of the records 1 and 3. Therefore, the candidate setting unit 18 keeps the record 2. The value of the record 3 is worse than the value of the record 2 with respect to the output variable 1, and is also worse than the value of the record 1 with respect to the output variable 2. Therefore, the candidate setting unit 18 sets the record 3 as a record to be deleted.

In this connection, the remaining records 1 and 2 are taken as the aforementioned "records with at least one good output variable".

At step S35, the candidate setting unit 18 generates twenty-fourth data D24 having N8 records regarding N1 input variables by applying the fourth approximate formulas to the twenty-third data D23 generated at step S34. Then, the process proceeds to step S36.

At step S36, the candidate setting unit 18 instructs the simulation unit 14 to run a computer simulation with the twenty-fourth data D24 generated at step S35. The simulation unit 14 runs the computer simulation with the twenty-fourth data D24, thereby generating twenty-fifth data D25 having N8 records regarding output variables. The simulation unit 14 returns the generated twenty-fifth data D25 to the candidate setting unit 18.

At step S37, the candidate setting unit 18 generates twenty-sixth data D26 for displaying scatter diagrams by combining the twenty-third data D23, twenty-fourth data D24, and twenty-fifth data D25. Then, the process of the candidate setting unit 18 is completed.

The candidate setting unit 18 according to the fourth embodiment is also capable of reducing the number of variables even if there are many variables to be displayed in scatter diagrams, which enables the user to more easily understand the results of multi-objective optimization.

(E) Fifth Embodiment

The following describes a computing apparatus according to a fifth embodiment.

The following mainly describes differential features of the computing apparatus of the fifth embodiment from the computing apparatus of the second embodiment, and description on the same features will not be repeated.

Figure 29:
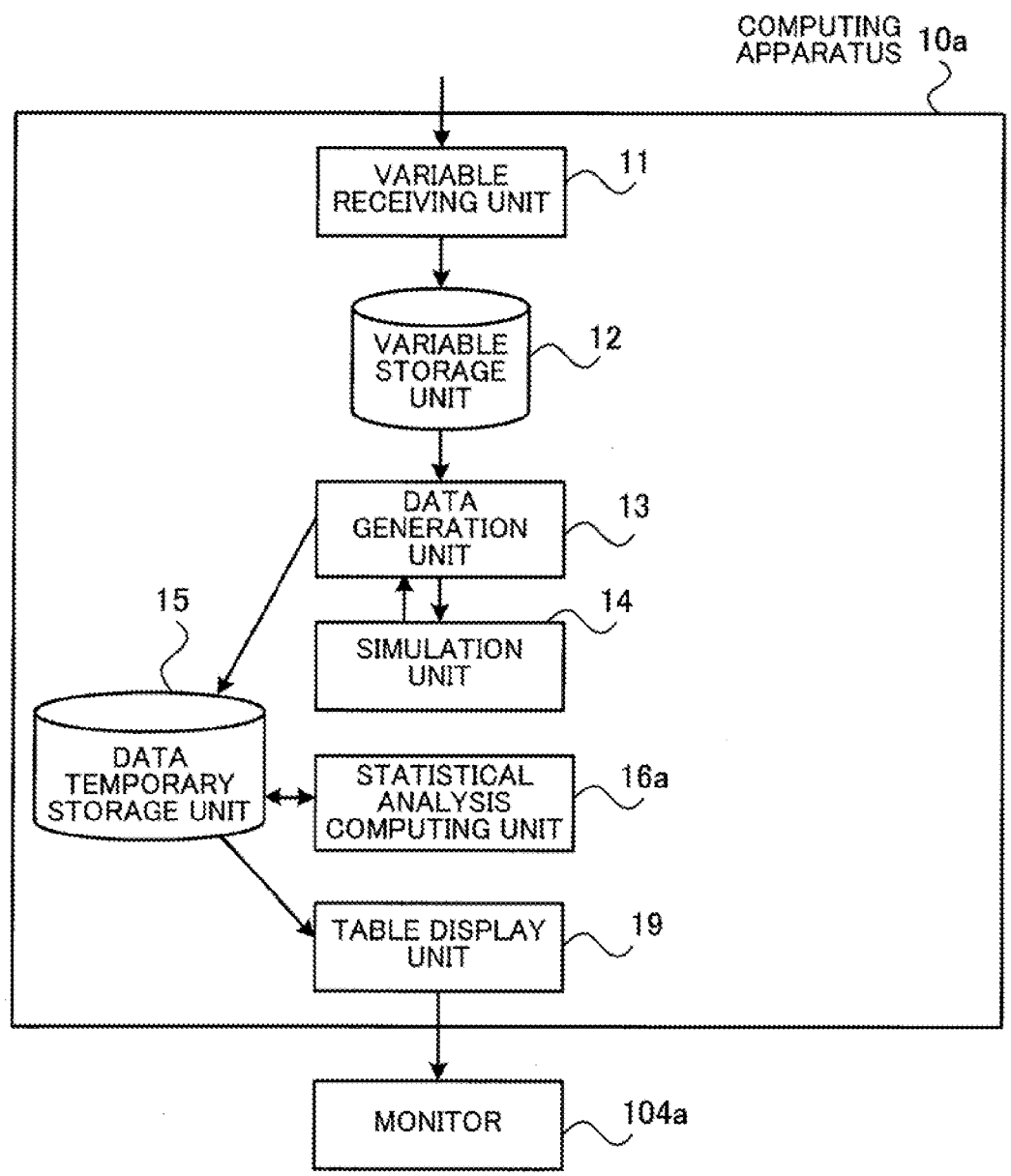
FIG. 29 is a functional block diagram of a computing apparatus according to a fifth embodiment.

FIG. 29 is a functional block diagram of a computing apparatus according to the fifth embodiment.

A computing apparatus 10a according to the fifth embodiment executes different statistical analysis computation.

A statistical analysis computing unit 16a executes statistical analysis computation for matrix visualization.

Figure 30:
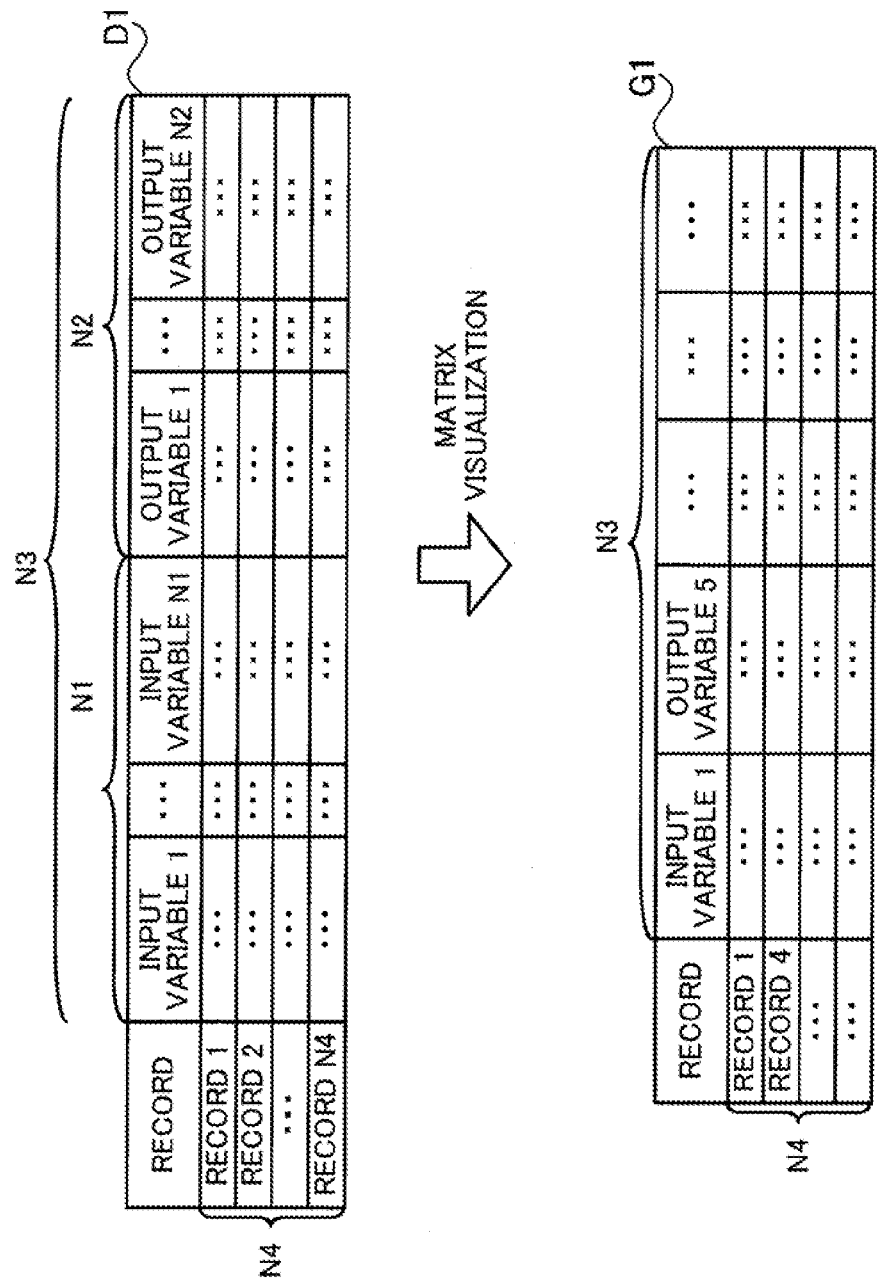
FIG. 30 is a diagram explaining a process of a statistical analysis computing unit according to the fifth embodiment.

FIG. 30 is a diagram explaining the process of a statistical analysis computing unit according to the fifth embodiment.

The statistical analysis computing unit 16a generates first data D1 in the same way as the second embodiment. Then, the statistical analysis computing unit 16a executes statistical analysis computation for matrix visualization with the first data D1. More specifically, the statistical analysis computing unit 16a creates a table G1 by soring the records of lines in such a way that similar records with respect to input variables and/or output variables are arranged next to each other and then soring the input and output variables of columns in such a way that input variables and output variables having similar values are arranged next to each other. Then, a table display unit 19 displays the created table G1 on a monitor 104a.

The computing apparatus 10a according to the fifth embodiment also enables a user to more easily understand the results of multi-objective optimization.

Further, the user is able to comprehensively analyze the computation results by comparing a plurality of scatter diagrams with each other, for example, by comparing scatter diagrams created by the computing apparatus 10 of the second embodiment and scatter diagrams created by the computing apparatus 10 of the fourth embodiment.

The process performed by the computing apparatus 10, 10a may be performed by a plurality of apparatuses in a distributed manner. For example, a program for multi-objective optimization may be executed by using a PC cluster connected to a management computer and a plurality of analysis computers, a parallel computer, grid computer, cloud computer, Symmetric Multi-Processor (SMP) computer, multi-core computer, many-core computer, etc.

In the case of using a plurality of apparatuses to perform the process of the computing apparatus 10 in a distributed manner, the management computer performs the same processes as those of the data generation unit 13, statistical analysis computing unit 16, scatter diagram creation unit 17, and candidate setting unit 18 of the computing apparatus 10. Each of the plurality of analysis computers performs the same process as the simulation unit 14.

Heretofore, the computing methods and computing apparatuses according to the illustrated embodiments have been described, but are not limited thereto. The described components may be replaced with other components having equivalent functions or may include other components or processing operations. Where appropriate, other components and features provided in the embodiments may be combined in a different way.

In addition, desired two or more configurations (features) in the embodiments may be combined.

The above processing functions can be realized by using a computer. In this case, a program is prepared, which describes processes for the functions of the computing apparatus 1, 10, and 10a. A computer realizes the above processing functions by executing the program. The program describing the intended processes may be recorded on a computer-readable recording medium. Computer-readable recording media include magnetic recording devices, optical discs, magneto-optical recording media, semiconductor memories, etc. The magnetic recording devices include Hard Disk Drives, Flexible Disks (FD), Magnetic Tapes, etc. The optical discs include DVDs, DVD-RAMs, CD-ROM/RW, etc. The magneto-optical recording media include MOs (Magneto-Optical disk), etc.

To distribute the program, portable recording media, such as DVDs and CD-ROMs, on which the program is recorded, may be put on sale. Alternatively, the program may be stored in the storage device of a server computer and may be transferred from the server computer to other computers through a network.

A computer which is to execute the above program stores in its local storage device the program recorded on a portable recording medium or transferred from the server computer, for example. Then, the computer reads the program from the local storage device, and runs the program. The computer may run the program directly from the portable recording medium. Also, while receiving the program being transferred from the server computer, the computer may sequentially run this program.

In addition, the processing functions may also be implemented wholly or partly by using a digital signal processor (DSP), application-specific integrated circuit (ASIC), programmable logic device (PLD), or other electronic circuits.

According to one aspect, information which enables easy understanding of relationship among input and output variables is provided.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A computing method comprising:
calculating, by a processor, distances representing degrees of dissimilarity between different records included in a set of data, the records each being a combination of values of a plurality of input variables and values of a plurality of output variables produced by a computer simulation using the values of the input variables, wherein the values of the input variables are obtained as a result of multi-objective optimization performed with respect to the computer simulation;
producing, by the processor, coordinates from the calculated distances between the records, the coordinates representing relative positional relationships among the records;
creating, by the processor, scatter diagrams for the respective input variables and output variables, the scatter diagrams each plotting samples representing values of the input variables and output variables at the coordinates produced for the records corresponding thereto;
displaying, by the processor, the created scatter diagrams;

dividing, by the processor, a region of the scatter diagrams into subregions, and generating intersection coordinates that indicate positions of intersection points of the subregions in the scatter diagrams;

calculating, by the processor, approximate values of the output variables by using approximate formulas for approximating the output variables, based on the generated intersection coordinates;

selecting, by the processor, a subset of the generated intersection coordinates that matches better with a predetermined condition about the calculated approximate values than other generated intersection coordinates in terms of at least one of the output variables;

calculating, by the processor, approximate values of the input variables by using approximate formulas for approximating values of the input variables, based on the selected subset of the generated intersection coordinates;

generating, by the processor, values of the output variables for each of the intersection coordinates belonging to the selected subset, by executing the computer simulation using the calculated approximate values of the input variables; and creating, by the processor, a scatter diagram in which samples representing the generated values of the output variables are plotted at the positions of the intersection points.

* * * * *